(12) United States Patent
Pellenc et al.

(10) Patent No.: US 8,964,180 B2
(45) Date of Patent: Feb. 24, 2015

(54) SELF-CONTAINED AND PORTABLE OPTICAL SPECTROMETER

(75) Inventors: Roger Pellenc, Pertuis (FR); Jean-Marc Gialis, Cheval Blanc (FR); Jean-Louis Ferrandis, La Motte d'Aigues (FR); Antoine Bourely, La Tour d'Aigues (FR); Véronique Bellon Maurel, Grabels (FR); Jean-Michet Roger, Montpellier (FR)

(73) Assignee: Pellenc Societe Anonyme, Pertuis (FR)

( * ) Notice: Subject to any disclaimer, the term of this patent is extended or adjusted under 35 U.S.C. 154(b) by 344 days.

(21) Appl. No.: 13/394,495

(22) PCT Filed: Sep. 3, 2010

(86) PCT No.: PCT/FR2010/000599
§ 371 (c)(1),
(2), (4) Date: May 22, 2012

(87) PCT Pub. No.: WO2011/027052
PCT Pub. Date: Mar. 10, 2011

(65) Prior Publication Data
US 2012/0229809 A1  Sep. 13, 2012

(30) Foreign Application Priority Data

Sep. 7, 2009  (FR) ..................... 09 04241

(51) Int. Cl.
| G01J 3/46 | (2006.01) |
| G01N 21/47 | (2006.01) |
| G01N 21/31 | (2006.01) |
| G01N 33/02 | (2006.01) |

(52) U.S. Cl.
CPC .............. G01N 21/474 (2013.01); G01N 21/31 (2013.01); *G01N 33/025* (2013.01); *G01N 2021/3177* (2013.01); *G01N 2201/0221* (2013.01)
USPC .......................................... 356/402

(58) Field of Classification Search
USPC .................................................. 356/300–334
See application file for complete search history.

(56) References Cited

U.S. PATENT DOCUMENTS

| 6,014,222 A | 1/2000 | Borggaard et al. |
| 2004/0149916 A1 | 8/2004 | Benedetti et al. |
| 2006/0158648 A1* | 7/2006 | Matthiessen et al. ......... 356/326 |

FOREIGN PATENT DOCUMENTS

| WO | 98/38494 | 9/1998 |
| WO | 02/088678 | 11/2002 |

OTHER PUBLICATIONS

M. Larrain et al., "Amultipurpose portable instrument for determining ripeness in wine grapes using NIR spectroscopy", IEEE Transaction on Instrumentation and Measurement, 2008, pp. 294-302, vol. 57, No. 2.

(Continued)

*Primary Examiner* — Tarifur Chowdhury
*Assistant Examiner* — Abdullahi Nur
(74) *Attorney, Agent, or Firm* — Greenblum & Bernstein, P.L.C.

(57) ABSTRACT

The invention relates to a portable and self-contained optical spectrometer for analyzing a light spectrum backscattered by an illuminated sample, in order to deduce the content of at least one compound constituting the sample, said spectrometer being arranged about an optical axis and including: a target area centered on said optical axis; a plurality of optical sensors trained on the target area; an opaque measurement chamber including: an opening centered on said optical axis; at least one diffusing filter blocking said opening; and an inner bottom capable of housing the plurality of optical sensors and a main illumination device capable of illuminating the sample. The invention further relates to a method for using such a spectrometer.

16 Claims, 17 Drawing Sheets

(56) References Cited

OTHER PUBLICATIONS

V. Geraudie et al., "A revolutionary device for predicting grape maturity based on NIR spectrometry", Frutic 09, 8th fruit nut and vegetable production engineering symposium, Sep. 5, 2009, pp. 1-8.

Blakey et al., "The potential of near-infrared spectroscopy in the avocado industry", South Africa Avacado Growers Association Yearbook, 2008, pp. 47-50, vol. 31.

C. Du Plessis, "Optimum maturity and quality parameters in grapes", , 1984, pp. 35-42, vol. 5, No. 1.

* cited by examiner

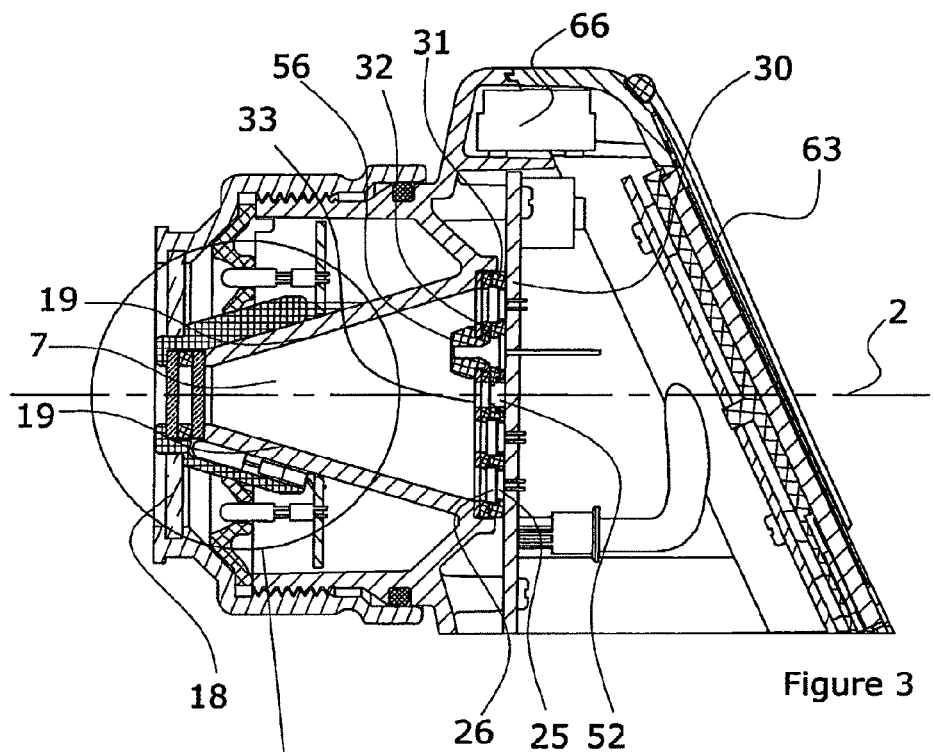
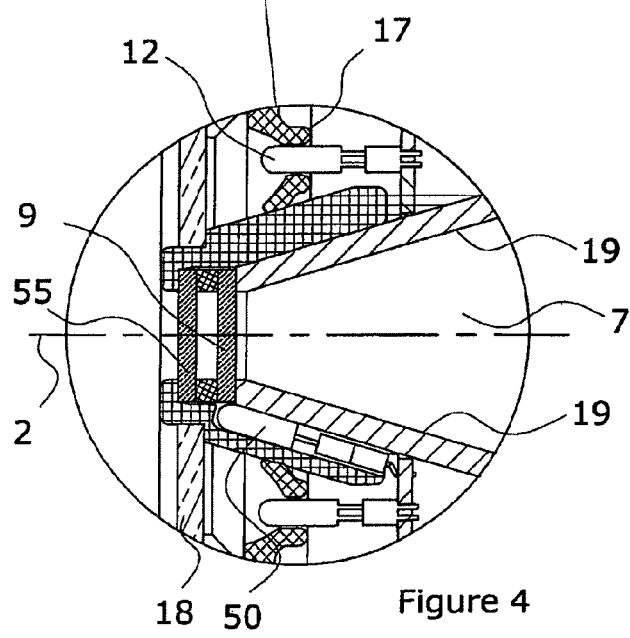
Figure 3
Figure 4

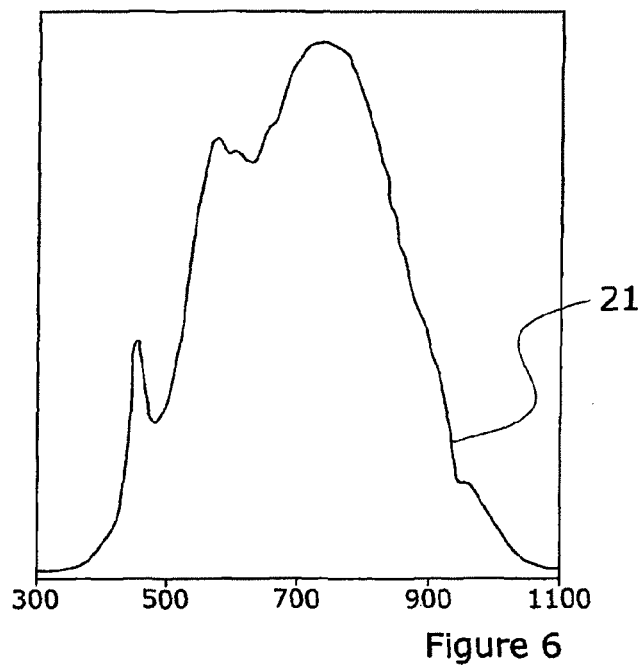
Figure 6
Figure 7
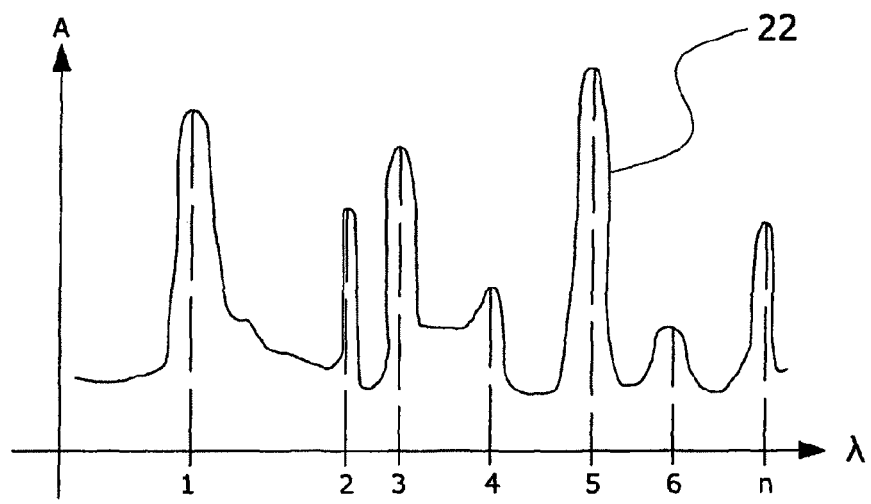

SELF-CONTAINED AND PORTABLE OPTICAL SPECTROMETER

The present invention relates to an optical spectrometer, particularly a self-contained and portable optical spectrometer, for analyzing the light spectrum backscattered by a sample subjected to lighting, in order to determine the content of at least one constituent compound of the sample.

In the content analyzing of the content of a compound in a sample of matter, it is known to perform a determination using a mass spectrometer, an optical spectrometer, or chromatography. These measurement principles require laboratory equipment, which is highly general-purpose, heavy and expensive.

A great many users nowadays need to be able to carry out analyzes of the aforementioned type quickly, directly in the field. In the food industry, reference can be made to viticulture, in which monitoring grape maturity by measuring changes in sugar, acid or anthocyanin content, preferably at the vineyard, makes it possible to determine an optimal date for the harvest. Mention can also be made of viniculture, in which it is advantageous to measure changes in the alcohol content to monitor the fermentation process. Oleiculture is another area of application, in which monitoring olive maturity by measuring the oil and water content in the olive, while on the tree if possible, makes it possible to determine an appropriate time for the harvest. Similarly, the measurement of sugar content in a fruit, such as an apple, a pear, a melon, etc., makes it possible to assess maturity and to determine an optimal harvest date. One can also mention the major cereal crops, in which measurement of nitrogen content in a leaf makes it possible to determine a reasoned application of nitrogen fertilizer.

The examples cited herein come from the food industry, but reference could be made to examples from other industries, such as the petrochemical industry (analysis of hydrocarbon contents), the medical diagnosis (measurement of blood sugar levels in diabetics), etc.

Viticulture is now subject to a growing demand for optimizing efficiency and quality so as to adapt production to market demands and consumer expectations. To meet this requirement, one solution is to assess grape ripeness criteria more efficiently in order to predict an optimum harvest date.

Maturity monitoring tests are performed from veraison to maturity of the grapes. These tests currently require grape or berry sampling from various plots. The samples are then sent to laboratories for analysis. The measurements thus performed are burdensome and costly. They require the samples to be destroyed. Sample collection is time-consuming. Laboratory analyzes are expensive. Furthermore, this procedure reveals maturity progress only in hindsight.

Therefore, there appears to be a need for a portable, self-contained, field-usable apparatus that is capable of collecting the content measurements of certain selected compounds, carried out directly on a product.

The present invention makes it possible to meet this need by providing a self-contained, portable optical spectrometer capable of measuring the contents of one or more configurable compounds, directly on the product, without requiring said product to be destroyed.

The object of the invention is an optical spectrometer, in particular self-contained and portable, adapted to analyze a light spectrum that is backscattered by an illuminated sample, in order to deduce the content of at least one constituent compound of the sample, said spectrometer being arranged about an optical axis and including:

a target zone centered on said optical axis and capable of receiving said sample,
a plurality of sensors including at least one optical sensor trained on the target zone,
a light-opaque measurement chamber including:
an opening centered on said optical axis,
at least one scatter filter blocking said opening,
an inner bottom centered on said optical axis and capable of housing said plurality of optical sensors,
said target zone being located in the vicinity of said opening, outside of the measurement chamber,
a main illumination device adapted to illuminate said sample.

According to another characteristic of the invention, the main illumination device is arranged, relative to the plane perpendicular to the optical axis passing via the scatter filter, on the side opposite the target zone.

According to another characteristic of the invention, the opening angle of the measurement chamber, starting from the opening, is less than or equal to the scatter angle of the scatter filter.

According to another characteristic of the invention, the inner bottom has a spherical shape centered on the target zone, or a planar shape perpendicular to the optical axis.

According to another characteristic of the invention, the measurement chamber has a photometric gain G at least equal to 4.

According to another characteristic of the invention, each optical sensor is capable of measuring luminous intensity along a given wavelength.

According to another characteristic of the invention, each optical sensor further includes an amplifier having a gain that is adjusted so as to maximize the excursion of the luminous intensity measurement.

According to another characteristic of the invention, the spectrometer further includes a reference illumination device, reproducing the luminous characteristics of the main illumination device and arranged outside of the measurement chamber so as to illuminate the inner bottom directly through the scatter filter.

According to another characteristic of the invention, the spectrometer further includes a system for measuring the color of the sample, including a third illumination device and an optical color sensor, both trained on the target zone.

According to another characteristic of the invention, the spectrometer further includes a system for fluorescence measurement of the sample, including a fourth illumination device and a specific optical sensor, both trained on the target zone.

According to another characteristic of the invention, the spectrometer further includes a logic processing unit capable of selectively switching on the illumination devices, and of acquiring, processing, storing and restoring the measurements and determinations obtained via processing based on these measurements from the optical sensors, the optical color sensor and the specific optical sensor, as well as a man-machine interface, interfaced with said logic processing unit capable of trigging a sequence of measurements and of displaying the results.

According to another characteristic of the invention, the spectrometer further includes a geolocation device.

According to another characteristic of the invention, the spectrometer further includes a device for transmitting information.

The invention further relates to a method for using such an optical spectrometer, including a step of obtaining a "real" measurement $m_i$ by acquisition, where the index i defines from 1 to n the plurality of optical sensors, in the presence of a sample in the target zone, only the main illumination device being switched on.

According to another characteristic of the invention, the method further includes a step of obtaining a "black" measurement $b_i$ by acquisition, where the index i defines from 1 to n the plurality of optical sensors, all of the illumination devices being switched off.

According to another characteristic of the invention, the method further includes a step of obtaining a "reference" measurement $r_i$ by acquisition, where the index i defines from 1 to n the plurality of optical sensors, only the reference illumination device being switched on.

According to another characteristic of the invention, the method further includes a step of determining a corrected value $X_i$ for i between 1 and n, such that $$X_i = \frac{m_i - b_i}{r_i - b_i}.$$

According to another characteristic of the invention, the method further includes a second derivation step, in order to obtain $D_i$ for i between 1 and n, such that $D_1=2(X_1-X_2)$, $D_i=2X_i-X_{i-1}-X_{i+1}$ for i between 2 and n−1, $D_n=2(X_n-X_{n-1})$.

According to another characteristic of the invention, the method further includes a normalization step, in order to obtain $N_i$, for i between 1 and n, such that $$N_i = \frac{D_i}{\sqrt{\sum_{i=1}^{n}(D_i)^2}}.$$

According to another characteristic of the invention, the method further includes a step of determining of the compound content $M_j$ in the sample, where the index j defines from 1 to p all of the compounds, the contents of which are measured, by applying the formula:

$$M_j = SM_{jn+1} + \sum_{i=1}^{n} N_i \cdot SM_{ji}$$

where $SM_{ji}$ is a characteristic coefficient.

An advantage of the spectrometer and the method according to the invention is in providing a portable and self-contained apparatus which is suitable for use in the field to produce immediately usable measurements, in a non-destructive manner, with an accuracy comparable to that of laboratory equipment, and which makes it possible to measure very low compound contents.

Other characteristics, details and advantages of the invention will become more apparent from the following detailed description, provided by way of example only, with reference to the annexed drawings in which:

FIG. 1 shows a detailed diagram of the optical principles used;

FIG. 2 schematically outlines the geometry of a spectrometer according to the invention;

FIG. 3 shows a cross-sectional view of a spectrometer according to a first embodiment;

FIG. 4 is detailed view of the opening of the spectrometer of FIG. 3;

FIG. 6 shows an illumination spectrum;

FIG. 7 shows a backscattered spectrum;

FIGS. 23 and 24 show the characteristic coefficients of two applications.

Reference is now made to the drawings to describe advantageous but non-limiting examples of embodiments of the optical spectrometer, and of the implementation of the method according to the invention.

Figure 1:
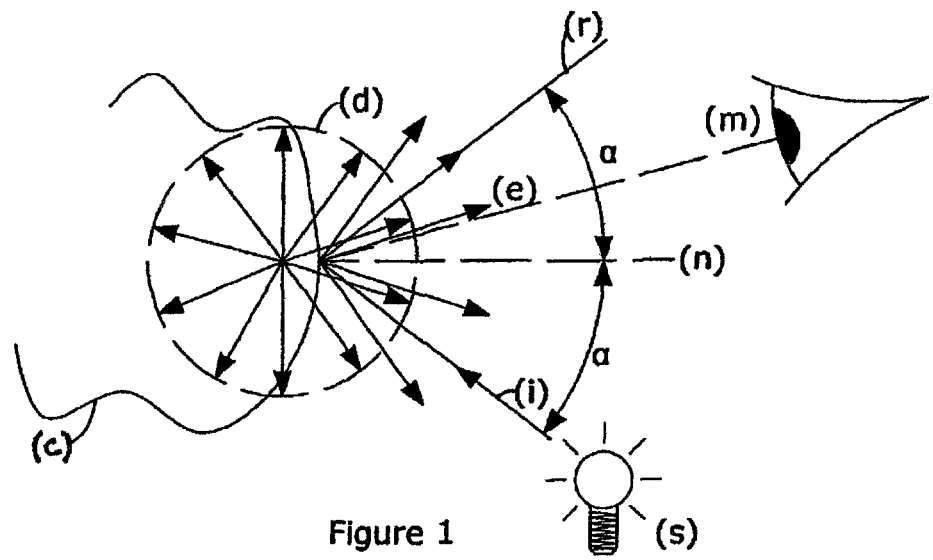

FIG. 1 illustrates an optical principle. A body c illuminated by a ray of incident light i, coming from a light source s, reflects this light according to at least three modes.

In a first "specular" mode, a reflected ray r is mainly concentrated along a preferred direction. This direction, determined by the laws of Descartes, is symmetrical with respect to the normal n to the surface of the body c at the point of impact of the incident ray i. The angle between the incident ray i and the normal n is equal to the angle between the normal n and the specular reflected ray r. In a second "diffuse" mode, the light is substantially uniformly backscattered d in all spatial directions. The invention takes advantage of this second mode. It has the advantage of allowing measurement by positioning a sensor m in any spatial direction while maintaining the ability to observe the same signal. One drawback is that the intensity of this signal is weak relative to the specular reflected signal r. Therefore, the present invention has a plurality of characteristics for improving the quality of the measurement in order to compensate for the relative weakness of the received signal. However, to observe this diffuse mode, one should not position a sensor in the direction of specular reflection r in order to avoid the risk of blinding/saturating it, due to the differences in the order of magnitude of the luminous intensities.

Unlike the specular mode, whereby reflection occurs on the surface of the object, the diffuse mode involves a certain penetration of the light within the body c. Depending upon the composition of the body c, the light spectrum is modified due to differential attenuations, as a function of the wavelengths. Thus, an essential property is that the wavelength spectrum of a signal backscattered by a sample is modified as a function of the compounds present in the sample, which selectively absorb certain wavelengths characteristic of said compounds.

The measuring principle of the spectrometer 1 according to the invention takes advantage of this property. It involves illuminating actively, with a light source of known spectrum 21, a sample 4 arranged in a target zone 3, and measuring the reflected light as backscattered by the sample 4 using optical sensors 5 in order to identify and characterize the backscattered spectrum 22. A modification of the backscattered spectrum 22 relative to the lighting spectrum 21 is then determined from this measurement. The analysis of this modification, by quantifying the attenuations that can be observed along certain characteristic wavelengths, makes it possible to deduce the contents of certain constituent compounds of the sample 4.

A third "surface" reflection mode, due to the micro surface roughness, also exists and is used for observing color.

Figure 2:
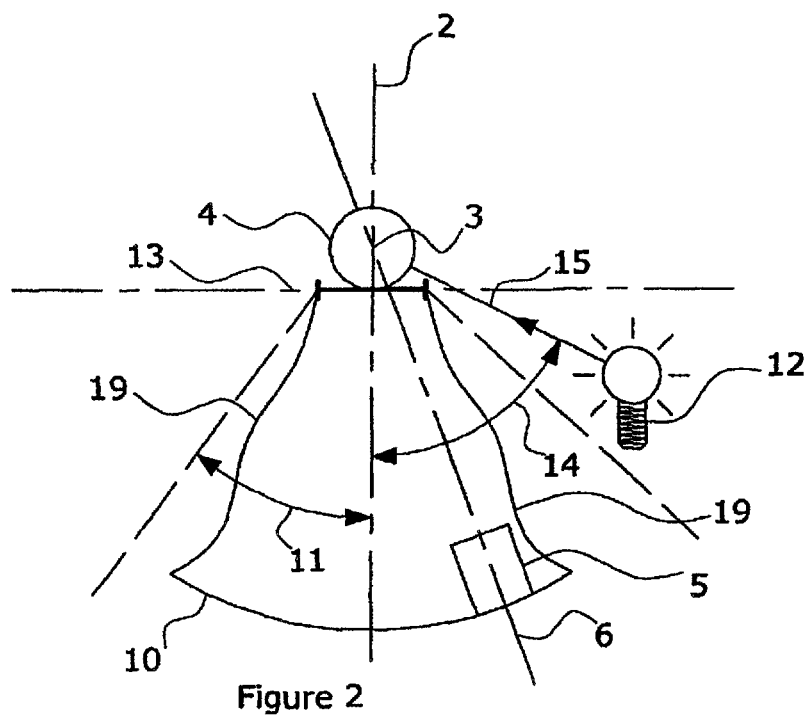

FIG. 2 schematically defines the geometry of an optical spectrometer 1 according to the invention, whereas FIGS. 3 and 4, and 5 and 6, respectively show a first and second illustrative mode of embodiment of such an optical spectrometer 1. The optical spectrometer 1 is arranged about an optical axis 2. A target zone 3, centered on said optical axis 2, on the periphery of the spectrometer, is free and accessible to permit the insertion of a sample 4 to be analyzed. The size of this target zone 3 is adapted to the products that one wishes to analyze. Its center 3 is located at the intersection of the optical axis 2 and of the axes 6 of the optical sensors 5. Its spatial extent varies depending upon the types of samples 4 processed and the optical characteristics of the spectrometer. The sample 4 can be solid or liquid.

The optical spectrometer 1 includes a plurality having at least one optical sensor 5. Each optical sensor 5 is trained on the target zone 3. In other words, its optical axis 6 passes through the target zone 3.

The optical spectrometer 1 further includes a measurement chamber 7 that is generally opaque to light, with the exception of an opening 8.

This opening 8 is centered on the optical axis 2, and it is the only light inlet pathway from the outside inward of the measurement chamber 7. The target zone 3 is close to the opening 8, while remaining outside of said opening 8 and the measurement chamber 7.

The opening 8 is also completely blocked by at least one scatter filter 9. Thus, any light entering the measurement chamber 7 from the outside becomes scattered upon crossing through said scatter filter 9. It is thus homogenized within the measurement chamber 7. A light measurement can thus be carried out in an identical fashion at any point in the measurement chamber 7, which allows great flexibility for positioning an optical sensor 5 within the measurement chamber 7.

To optimize the luminous power entering the measurement chamber 7, the scatter filter 9 has a very low attenuation. The target zone 3 is limited by the outer surface of the scatter filter 9. The outer surface of the scatter filter 9 also provides a bearing surface allowing contact with the sample 4 during a measurement sequence. The scatter filter 9 further protects the inside of the measurement chamber 7 against possible insertion of solid or liquid foreign bodies.

The measurement chamber 7 further includes an inner bottom 10. This inner bottom 10 is centered on the optical axis 2 and has a surface capable of receiving the plurality of optical sensors 5.

To illuminate the sample 4 actively, with a light source of known spectrum 21, the spectrometer 1 includes a main illumination device 12. This main illumination device 12 is capable of illuminating the sample 4. It is positioned outside of the measurement chamber 7.

The function of the main illumination device 12 is to illuminate the sample 4, with sufficient intensity to produce a diffuse reflection that can be measured by the plurality of optical sensors 5.

The direction of the main illumination device 12, relative to the optical axis 2 to produce a diffuse reflection towards the measurement chamber 7, can be any direction since the diffuse reflection is omnidirectional. However, it is preferable for the main illumination device 12 not to illuminate the opening 8 in direct view, in order not to disrupt the optical sensors 5 with a much stronger signal than that, backscattered, which is to be measured. For this, the main illumination device 12 must at least be arranged, on the side opposite the target zone 3, relatively to the plane 13 perpendicular to the optical axis 2 and passing through the scatter filter 9 (said plane coincides with the plane of the opening 8 and the positioning plane of the sample 4).

Because one wishes to exploit the diffuse reflection, which is of relatively lower intensity than the specular reflection, it is necessary to ensure that a specular reflection does not enter the measurement chamber 7 (via the opening 8), as this would substantially disrupt the measurement by blinding the optical sensors 5. This is achieved by the previously described positioning of the main illumination device 12, in cooperation with a positioning of the sample pressed against the plane 13. In addition to its main function described hereinabove, the scatter filter 9 fulfills a secondary function of scattering a possible specular reflection entering the measurement chamber 7. This scattering substantially attenuates the consequences of such a reflection. As a last resort, an acceptance test, described hereinafter, makes it possible, if necessary, to detect the presence of an anomaly caused by such specular reflection in the measurement.

The wavelengths are not modified between the emission by the illumination device 12 and the backscatter; only the light intensity is more or less attenuated depending upon the particular absorption wavelengths of the constituent compounds of the sample 4. The light spectrum 22 backscattered in the measurement chamber 7 is analyzed using optical sensors 5. The latter advantageously perform intensity measurements along certain especially selected discrete wavelengths. It is therefore necessary for the light spectrum 21 emitted by the illumination device 12 to contain all of the wavelengths for which attenuation is to be measured using the optical sensors 5. A first simple means is to use a main illumination device 12 having a broad spectrum including all of the specially selected wavelengths. It is however noted that an illumination comprising only such especially selected wavelengths at a minimum is sufficient. However, it is easier to achieve a wide spectrum illumination typically covering the wavelengths between 300 and 1800 nm. Such a spectrum thus covers all of the wavelengths corresponding to all of the compounds, the content of which one may wish to measure.

In the case of an illustrative application directed to grape ripening, a spectrum between 300 and 1100 nm is sufficient to cover the wavelengths selected.

A wide spectrum of this type can be obtained by any conventional illumination means, such as an incandescent bulb, a gas bulb, a light-emitting diode (LED), or any combination of these components.

The main illumination device 12 is advantageously in annular arrangement about the optical axis 2 in order to increase the amount of light illuminating the sample 4. It is advantageous to maximize this amount of light in order to enhance the sensitivity of the spectrometer 1, despite a low "yield" of the backscatter. A reflector 17, for example metallic and annular, can also be used in order to concentrate the luminous flux of the illumination in the direction of the target zone 3 and of the sample 4.

In one advantageous embodiment, the main illumination device 12 is protected by a protective wall 18. This wall is advantageously translucent and optically neutral to prevent a loss of luminous power. However, it makes it possible to protect the components of the main illumination device 12 against foreign bodies. This protective wall 18 is made, for example, of glass.

The function of the measurement chamber 7 is to receive the optical sensors 5. However, these optical sensors 5 cannot all be arranged in the same ideal measurement location. This is compensated for by the homogenization, achieved by at least one scatter filter 9, of any luminous signal entering the measurement chamber 7. In order for said scatter filter 9 to be efficient in its scattering function, the inner lateral wall 19 of the measurement chamber 7 can have any shape, provided that it is at least contained in a cone-shaped envelope, the opening angle 20 of which remains less than or equal to the scatter angle 11 of the scatter filter 9. Thus, as shown in FIGS. 8 to 11, this lateral wall 19 may be conical, cylindrical, spherical or the like.

The effect of homogenization by diffusion is further enhanced by an embodiment in which said inner wall 19 of the measurement chamber 7 is optically absorbent. This can be achieved, in a known manner, by a suitable material or coating.

It has been mentioned hereinabove that the optical sensors 5 are trained on the target zone 3. To enable easy implementation of the optical sensors 5 achieving this condition, a first embodiment ideally uses an inner bottom 10 of the measurement chamber 7 having the shape of a spherical cap, the center of this sphere being located in the area of the target zone 3. Thus, an optical sensor 5, mounted flat on the inner bottom 10, therefore has its optical axis 6, normal to the surface of the spherical cap, aligned with the target zone.

However, obtaining a spherical inner bottom 10 is complex, and a flat, simpler bottom is preferred. In this case, however, the optical axis 6 of an optical sensor 5 is all the more misaligned with the target zone 3 that the optical sensor 5 is mounted away from the optical axis 2. Two techniques are described hereinafter to correct/compensate for this axial misalignment.

To optimize the sensitivity of the spectrometer 1, it is necessary to maximize the light intensity received within the measurement chamber 7. In addition to retaining a scatter filter 9 having low attenuation and a powerful main illumination device 12 provided with a reflector, the geometry of the measurement chamber 7 can also be optimized. The proportion of said measurement chamber 7 is advantageously designed so as to have a maximum photometric gain G. The photometric gain G is defined by the formula:

$$G = 100 \cdot \left(\frac{\Phi}{L}\right)^2,$$

where $\phi$ is the diameter of the opening 8, and L is the distance between said opening 8 and the inner bottom 10. To increase G, it is possible to either increase $\phi$, or reduce L. In practice, a value of G at least equal to 4 is advantageously retained.

The diameter $\phi$ is related to the typical dimensions of the samples 4. The size of the inner bottom 10 is dependent upon the number of optical sensors 5 used. This number is dependent upon the contents that one wishes to measure.

The opening angle of the measurement chamber is at least equal to the scatter angle of the scatter filer 9. Too large an opening 11 for the measurement chamber 7 is detrimental in that a portion of the light entering the measurement chamber 7 is lost. Advantageously, the opening of the chamber is selected to be greater than but almost equal to the scatter angle of the scatter filter 9. The geometry of the measurement chamber 7 is thus determined, and a minimal length L respecting the previous angle condition is advantageously selected.

Thus in the case of an application to grapes, clusters of which are to be measured, the substantial dispersion of the sample sizes has experimentally led to retain an optimum diameter $\phi$ of 10 mm. The compounds retained require using 13 optical sensors 5, measuring 5×5 mm, which are positioned on an inner bottom 10 having a diameter of 36.5 mm. A scatter filter 9 having a scatter angle of 40° requires a minimum distance L of 50 mm, or a photometric gain substantially equal to 4.

To analyze the retroreflected light spectrum, the measurement chamber 7, and more particularly its inner bottom 10, is equipped with optical sensors 5. According to an important and advantageous feature of the invention, said retroreflected spectrum 22, an example of which is shown in FIG. 7 in comparison to the illumination spectrum 21 shown in FIG. 6, is analyzed using measurements of light intensity. In a particular embodiment, these measurements are performed on a set of discrete values of wavelengths selected as a function of the set of compounds whose content is to be determined. An optical sensor 5 is associated with each of the wavelengths, for measuring the luminous intensity in a narrow band centered on said wavelength. The choice of said wavelengths is advantageously obtained by an optimization that generally takes into account all of the compounds whose content is to be determined, and which is described hereinafter.

To obtain such an optical sensor 5 dedicated to a wavelength thus selected, the optical sensor 5 includes, for example, a photodiode 25 and an optical filter 26 that is arranged in front of a sensitive surface of said photodiode 25. Thus, said photodiode 25 measures only the luminous intensity received in a band around said wavelength. The photodiode can be of the silicon (Si) or Indium Gallium Arsenide (InGaAs) type. It is capable of outputting an analog electrical signal indicative of the luminous intensity received.

According to an advantageous embodiment, the photodiode 25 is a large area photodiode to improve the amount of light received. This contributes to improving the signal to noise ratio and the sensitivity of a spectrometer 1.

By combining the various geometrical, optical and electronic characteristics of the spectrometer, it is possible to obtain a signal to noise ratio of the luminous intensity measurements that is greater than or equal to 6000, and which makes it possible to determine very low compound content.

The optical filter 26 is advantageously a narrow band-pass filter centered on said wavelength. Filters having a bandwidth of 4 nm yield a satisfactory result. Advantageously, the optical filter 26 is sufficiently large to cover, as completely as possible, the sensitive surface of the photodiode 25, with which it is associated in order to maximize the luminous efficacy of the optical sensor 5. Advantageously, the optical filter 26 is closely pressed against the sensitive surface of the photodiode 25.

According to an advantageous embodiment shown in FIGS. 12 to 15, the optical sensors 5 are assembled and positioned via assembly of multiple parts. In a first embodiment, shown in FIGS. 12 and 13, a first rigid, substantially planar support part 30 receives the photodiodes 25 and ensures their accurate positioning. Advantageously, this part 30 can be a printed circuit board 30. The photodiodes are then welded into position and the printed circuit board further ensures the wiring of the photodiodes. A second rigid, substantially planar spacer part 31, in which housings are provided to receive the optical filters 26, ensures their positioning relative to the photodiodes 25 in the plane of assembly. A third intermediate, substantially planar part 32, made of an elastic material, is cut out so as to be superimposed on the support part 31. The cumulative thickness of the support part 31 and the intermediate part 32 is greater than the thickness of the optical filters 26 when the intermediate part 32 is at rest, and less than said thickness when the intermediate part 32 is compressed. A fourth tightening part 34 holds the assembly together. The fourth tightening part 34 comprises, in the area of the optical filters 26, cutouts that expose at least the sensitive surface of each photodiode 25, but cover the periphery of each optical filter 26 in order to ensure its retention. Compression of the intermediate part 32 ensures backlash elimination and presses the optical filters 26 against the photodiodes 25, along the direction of the axis 6 of the optical sensor, perpendicular to the plane of assembly.

Figure 14:
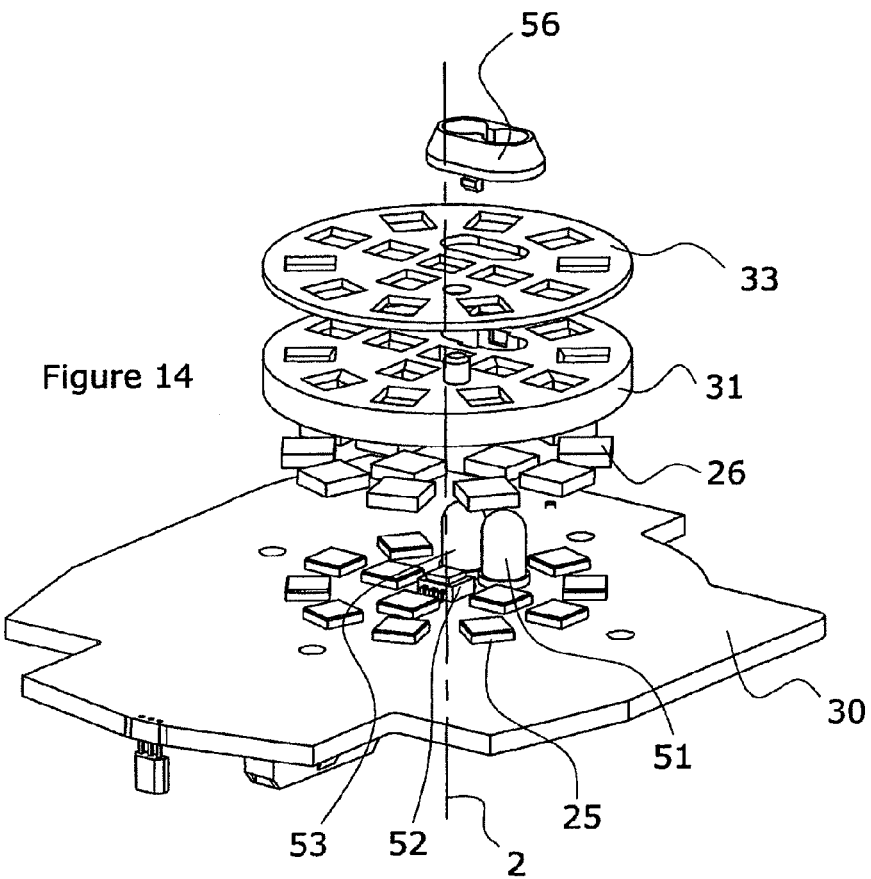
FIGS. 14 and 15 illustrate perspective views showing a device, exploded and assembled, respectively, for mounting the optical sensors, according to a second embodiment.
Figure 15:
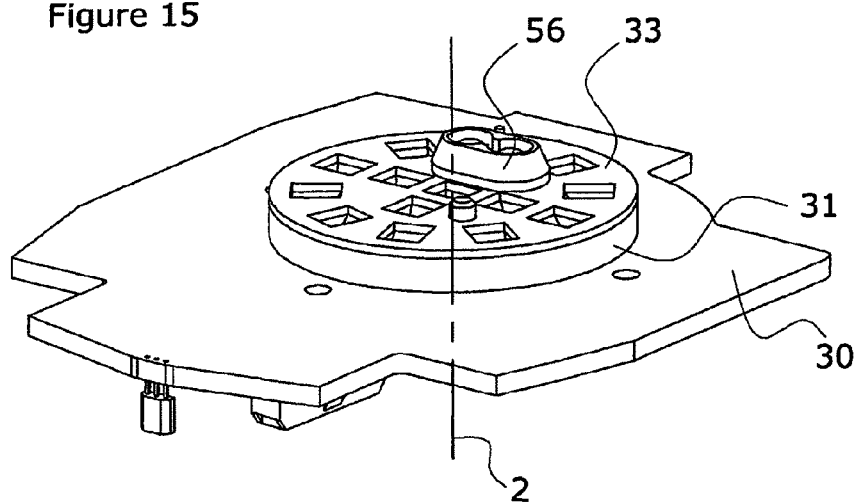

According to an alternative embodiment, shown in FIGS. 14 and 15, the spacer 31 and intermediate 32 parts are merged into a single elastic part 31 that fulfills their functions.

Figure 16:
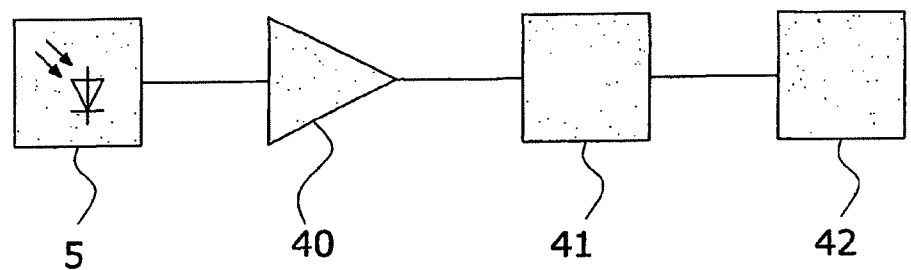
FIG. 16 shows a diagram of a measurement chain.
Figure 17:
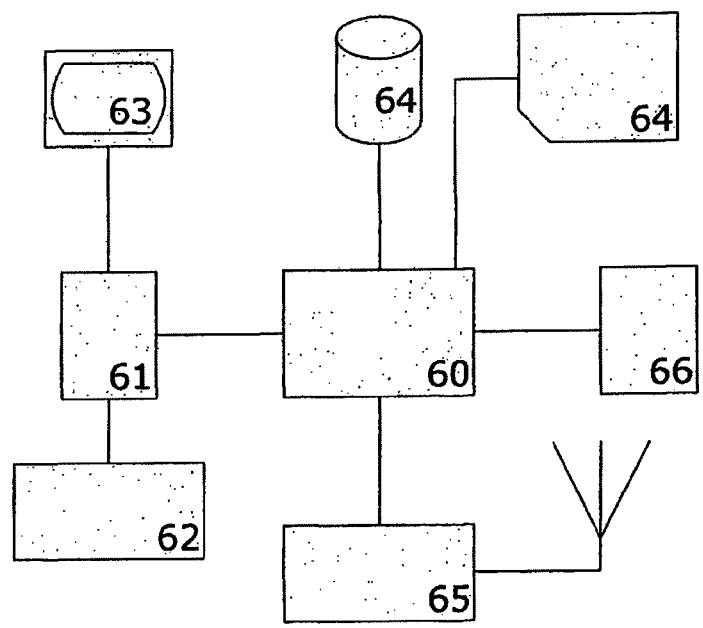
FIG. 17 shows a diagram of the computer system of the spectrometer.

FIG. 16 illustrates an embodiment of the processing chain associated with an optical sensor 5. Each sensor 5 is associated with an amplifier/filter 40, 41, for processing the output electrical signal of the optical sensor 5. This signal processing filter includes at least one amplifier 40. Advantageously, the gain of each amplifier 40, associated with an optical sensor 5, is adjustable separately, in order to allow maximizing the excursion of the measurement of the luminous intensity observable on this optical sensor 5, under normal conditions of measurement. For each optical sensor 5, depending upon the compounds, the content of which is to be determined, and upon the typical population of the probability sample, it is possible to determine a maximum value of the observable luminous intensity, with a safety margin, if necessary. The gain of the amplifier 40 is then adjusted so that this maximum intensity value corresponds to the maximum value of the measurement acceptable downstream by an acquisition device 42. This makes it possible to maximize the use of the signal measured by taking advantage of the dynamics of the processing device 42 downstream, in order to obtain high sensitivity and better signal to noise ratio.

The optical sensor processing chain can also include other components. It is thus possible to use filters 41 or other components, in order to carry out any preprocessing of the electrical measurement signal. The processing device 42 is advantageously a digital-to-analog converter 42 for interfacing with a logic processing unit 60 described hereinafter. Depending upon the number of optical sensors 5, it is also possible to use a multiplexer to multiplex said optical sensors 5 with said logic processing unit 60.

As seen hereinabove, it is advisable that the optical sensors 5 be trained on the target zone 3. A first embodiment with a spherical inner bottom 10 meets this requirement, but is difficult to implement, particularly in the preferred embodiment using a plane printed circuit board. A flat inner bottom 10 is therefore preferred. On a flat support bottom, however, the axis 6 of an optical sensor 5 is no longer trained on the target zone 3, and it is all the more misaligned with respect to a direction aiming at the target zone 3 that the optical sensor 5 is mounted away from the optical axis 2.

A first embodiment involves correcting said misalignment using an angular correction, for example by means of a slant support, radially arranged, for each optical sensor 5, the slant being a function of the distance to the optical axis 2, in order to reproduce the angle that the optical sensor 5 would present, if mounted on a spherical cap. However, such a correction is difficult to implement given the small angles to consider.

A second embodiment involves correcting no longer said misalignment but rather its consequence. An axial misalignment modifies the measured wavelength of the luminous signal in a known manner, by shifting it towards blue. Since the axial misalignment angle is known, its consequence on the measurement of the luminous signal can be corrected by shifting the wavelength associated with the optical sensor 5 by a value corresponding to said misalignment angle. This shift is achieved by the choice of the optical filter 26 during design. Thus, for a wavelength λ determined as a function of the compounds, the optical sensor is "adjusted" over a shifted wavelength λ' as a function of the wavelength λ and the distance (or misalignment angle of the axis 6) of the optical sensor 5 relative to the optical axis 2.

The wavelengths associated with said optical sensors 5 make it possible to characterize the backscattered light spectrum. The number and values of the wavelengths retained can be arbitrary. However, a judicious choice of this number and these values can markedly improve the quality of the measurements.

Thus, according to a preferred method, the number of wavelengths and the particular values of these wavelengths can be generally selected as a function of the set of compounds, the contents of which are to be determined.

An example of a method for determining the wavelengths is based on a global optimization obtained by maximizing an objective or performance function. Let's consider an extensive set of candidate wavelengths $\lambda_1 \ldots \lambda_m$. The cardinal m of this set can be very large. Thus, it is possible to start by including all of the wavelengths of the selected spectrum, with a given pitch of 1, 2 or several nm, or yet all of the commercially available wavelengths. Any selection S of n, n<m, wavelengths is considered in this set, and the objective function is calculated for this selection S. The objective function F is chosen such that its value F(S) is maximum when the optical sensors associated with the wavelengths selection S realize a minimum error, with a minimum number of wavelengths. An example of function is given by the formula:

$$F(S) = \sum_{i=1}^{n} \frac{E_i}{S_i},$$

where i is over the compounds, from 1 to k, to be predicted, $E_i$ is the prediction error obtained for the $i^{th}$ compound to be predicted, and $S_i$ is the standard deviation of concentration of this $i^{th}$ compound to be predicted.

The various selections S are then iterated over. A simplistic method iterates over all possible selections S. The one with ordinary skill in the art of global optimization methods knows heuristics that make it possible to substantially reduce the selections S retained, and thus the size of the research space.

For the illustrative example applied to grapes, the choice of the four compounds: water, sugar, polyphenols anthocyanins, acid, makes it possible to determine an optimal series of 13 "theoretical" wavelengths as follows: 440, 520, 665, 690, 740, 770, 805, 840, 875, 910, 945, 980 and 1015 nm.

Given that the first ten optical sensors (440 to 910 nm) are arranged on the printed circuit board 30, along a first outer crown, and have a resulting misalignment of 13.86°, and that the last three optical sensors (945 to 1015 nm) are arranged on the printed circuit board 30, along a second inner crown, and have a resulting misalignment of 6.81°, the "corrected" wavelengths become: 442, 522, 668, 693, 743, 773, 809, 844, 879, 914, 946, 981 and 1016 nm.

To improve the measurement quality of the spectrometer 1 of the invention, a compensation device is advantageously implemented. For this, the spectrometer 1 advantageously includes a reference illumination device 50. The objective of the reference illumination device 50 is to make it possible to carry out a reference measurement similar to the real measurement, except that the light is not backscattered by the sample 4. Thus, by comparing the two measurements obtained with and without attenuation by the sample 4, it is possible to determine the influence of sample 4, in terms of light attenuation, with greater precision.

This reference illumination device 50 is selected to emit a light spectrum as identical as possible to that emitted by the main illumination device 12. For this, the reference illumination device 50 emits, under comparable conditions of use, at any moment, a spectrum that has the same characteristics, despite the possible changes in the temperature of the illumination devices and despite their aging, as the spectrum 21 emitted by the main illumination device 12. One way to achieve this goal is to reproduce an identical structure of the main illumination device 12, by making a reference illumination device 50 comprised of the same number of components (bulbs, LEDs, etc.), of the same type, of the same reference, and of the same manufacturing batch as those of the main illumination device 12. However, this is especially true for the incandescent lamps. The LEDs can be considered as not being sensitive to temperature variations or aging. In practice, a main illumination device 12 can include incandescent lamps supported by LEDs in order to increase the luminous flux, whereas the reference illumination device 50 only includes incandescent lamps of the same type, same reference and same manufacturing batch.

One can also advantageously provide, with respect to the method of use, which will be described hereinafter, to control comparable durations for the respective switching on of the main illumination device 12 and the reference illumination device 50 so that, at the time they are used during the acquisitions, the illumination devices 12, 50 have identical temperatures and, therefore, spectra.

To reproduce a light, seen by the optical sensors 5, that is comparable to that coming from the main illumination device 12, the reference illumination device 50 is arranged outside of the measurement chamber 7, so that its light illuminates the inner bottom 10 of the measurement chamber 7, in which the optical sensors 5 are arranged, after being scattered by the scatter filter 9. A possible arrangement is illustrated in FIGS. 3 and 4, in which the reference illumination device 50 is arranged on the edge of the scatter filter 9.

The optical spectrometer 1 according to the invention further advantageously includes other optical sensors in order to perform other measurements simultaneously on the same sample 4.

Thus, the optical spectrometer 1 can include a system 51, 52 for measuring the color of the sample 4. This system includes a third illumination device 51 and an optical color sensor 52. This color measurement system operates according to the third mode of surface reflection. It is advisable that the illumination axis of the sample 4 and the color measurement axis be arranged symmetrically to one another with respect to the optical axis 2, assuming that the sample 4, pressed against the plane of the opening 8 in the area of the target zone 3, has a normal parallel to said optical axis 2. A configuration necessary to achieve this condition is that both the third illumination device 51 and the optical color sensor 52 are trained on the target zone 3.

According to a first embodiment, illustrated in FIGS. 3 and 4, the third illumination device 51 and the optical color sensor 52 are arranged on the inner bottom 10.

According to a second embodiment, the opening 8 of the measurement chamber 7 is equipped with a lens 55 blocking the opening 8 on the outside relative to the scatter filter 9, and the third illumination device 51 and the optical color sensor 52 are arranged between the scatter filter 9 and the lens 55. Such a configuration is shown, for example, in FIG. 5. The target zone 3 is located outside of this lens 55, according to this embodiment. This lens 55 then replaces the scatter filter 9 in its functions of supporting the sample 4 and protecting the measurement chamber 7 against foreign bodies.

This lens 55 can be made of an optically neutral translucent material such as glass. This lens 55 can also advantageously be a second scatter filter.

The third illumination device 51 is advantageously a wide spectrum light source, comparable to the main illumination device 12. This can be an LED emitting a white spectrum to reduce the occupied space. A cover 56 advantageously makes it possible not to directly illuminate the adjacent optical color sensor 52.

In a known manner, the optical color sensor 52 measures the intensities based on three colors, typically red, green and blue. The optical color sensor 52 includes three individual sensors each measuring one of the three colors retained. These three sensors can be further integrated into a single component.

The optical spectrometer 1 can further include a system 53, 54 for the fluorescence measurement of the sample 4.

This system includes a fourth illumination device 53 and a specific optical sensor 54. The fluorescence measurement system 53, 54 operates by reemission. The fourth illumination device 53 and the specific optical sensor 54 are trained on the target zone 3.

Similarly, the fluorescence measurement device can be arranged on the inner bottom 10, according to a first embodiment. It is advantageous that both the fourth illumination device 53 and the specific optical sensor 54 be arranged on the inner bottom 10, in coincidence with the optical axis 2.

Figure 5:
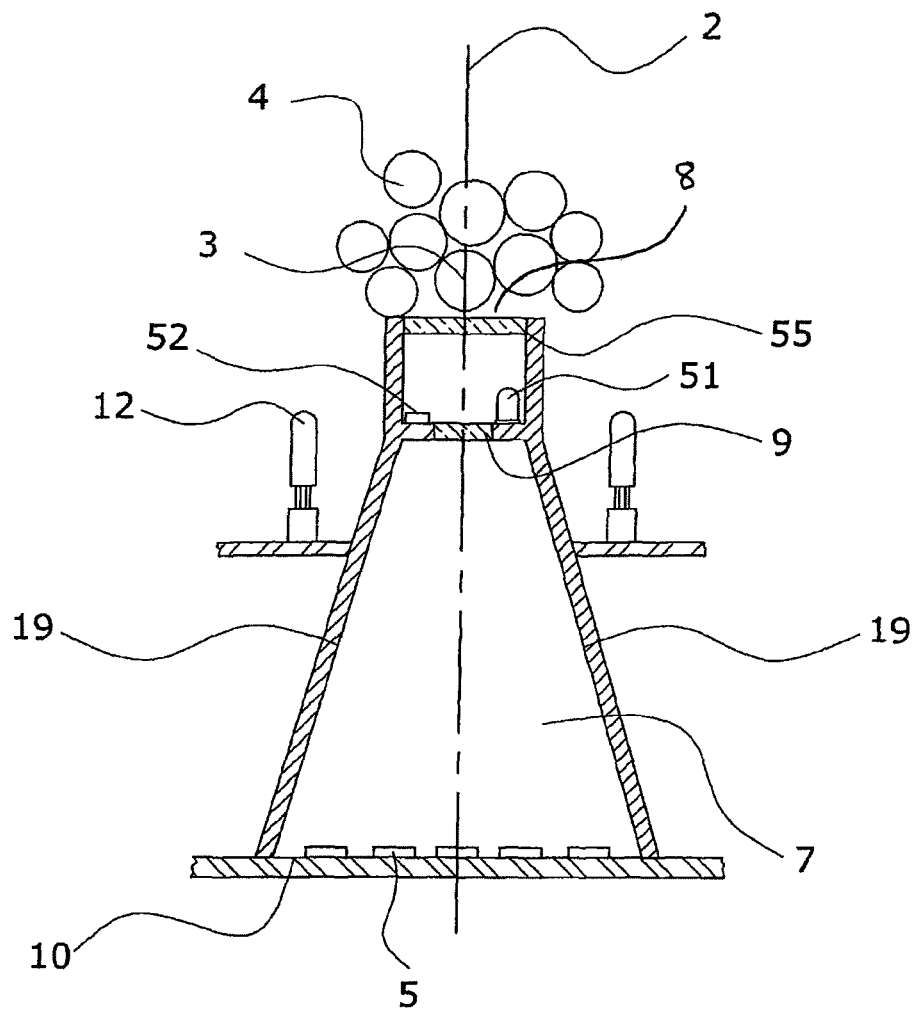
FIG. 5 shows a cross-sectional view of a spectrometer according to a second embodiment.
Figure 8:
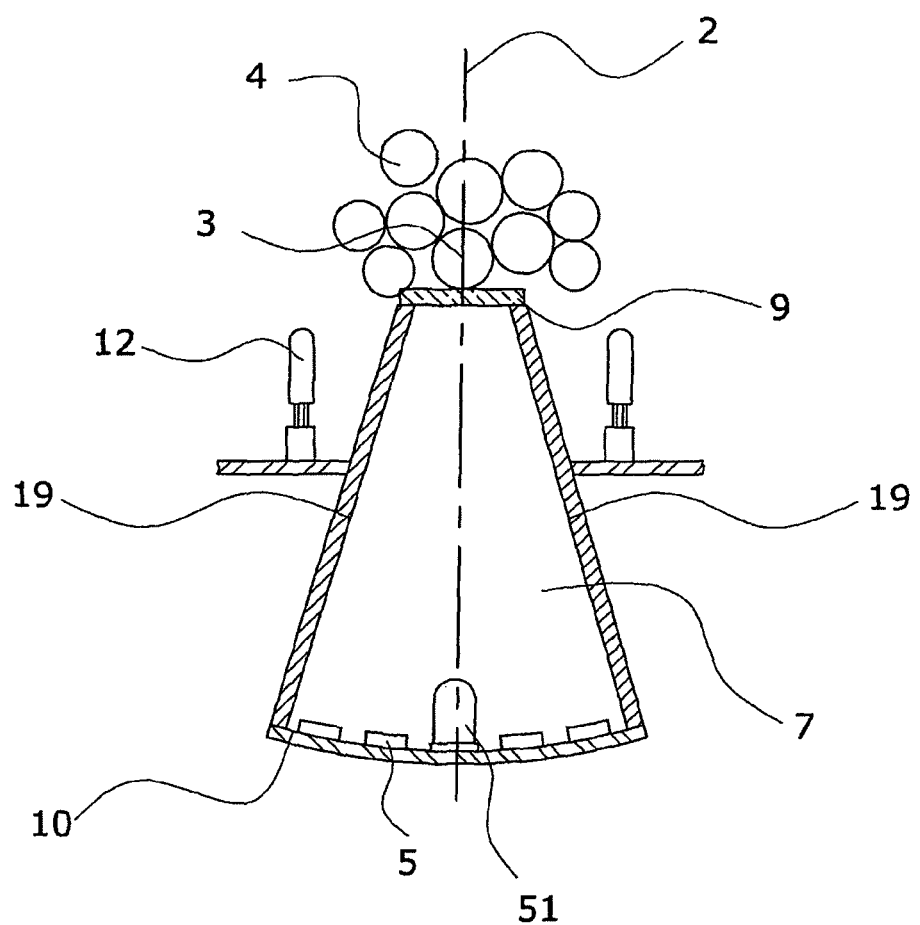
FIGS. 8 to 11 show four configurations of the measurement chamber.
Figure 9:
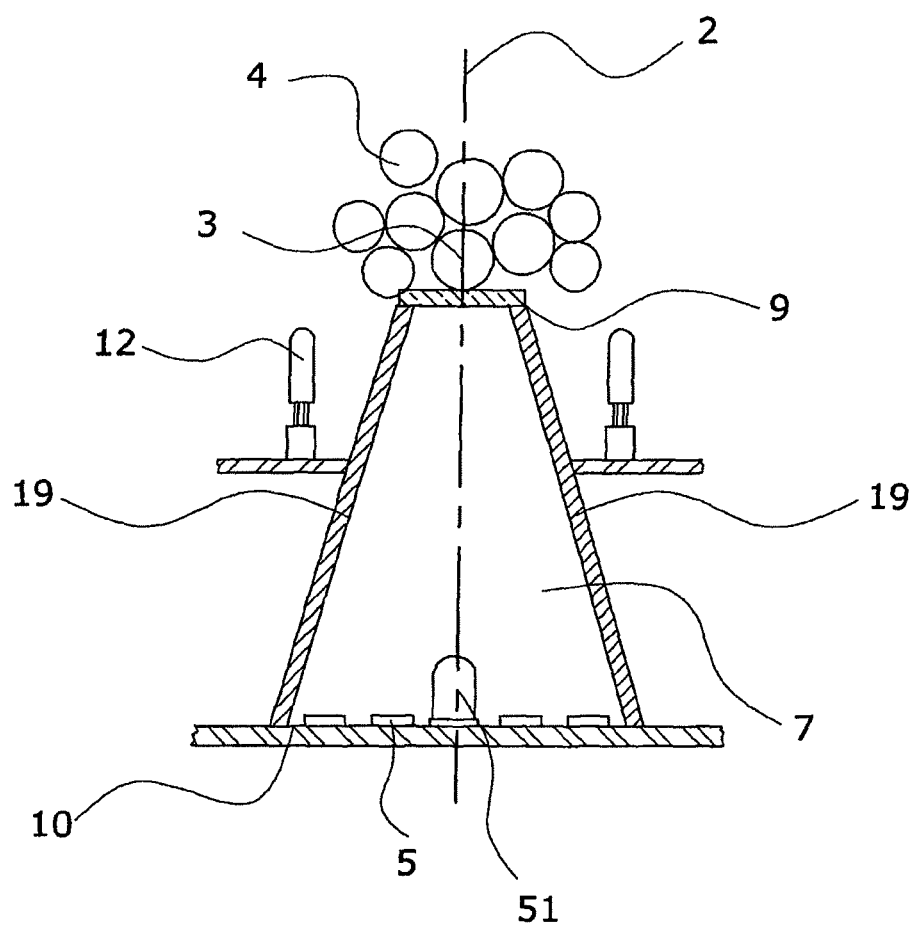
Figure 10:
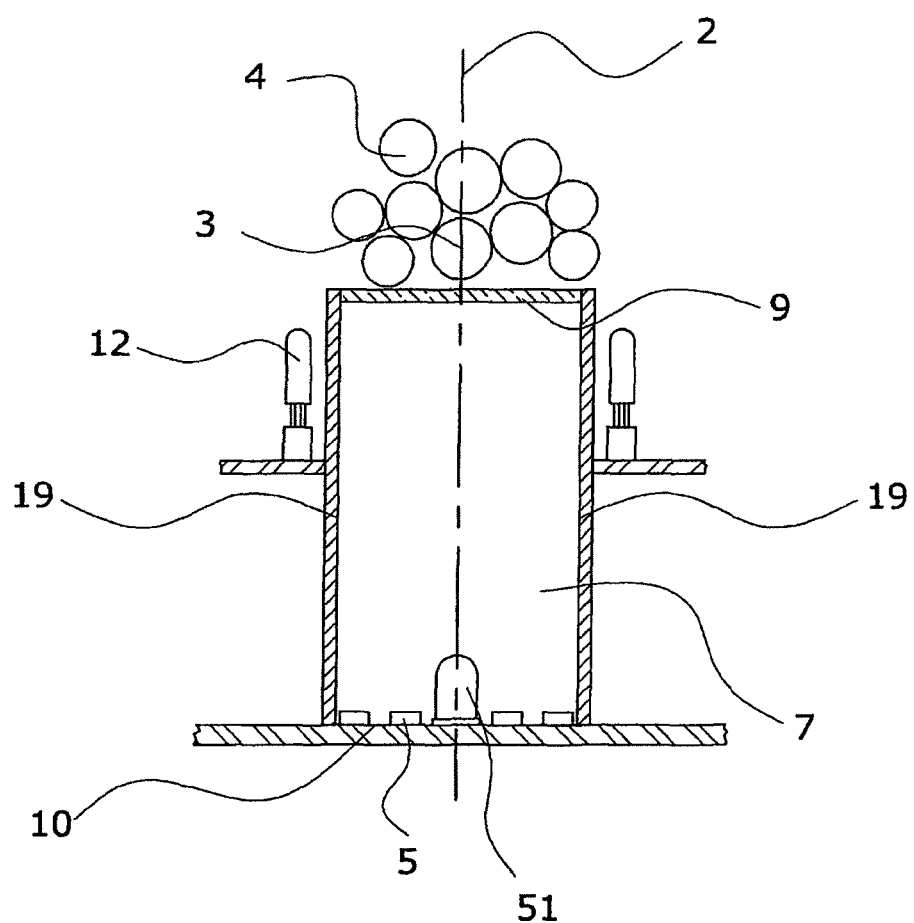
Figure 11:
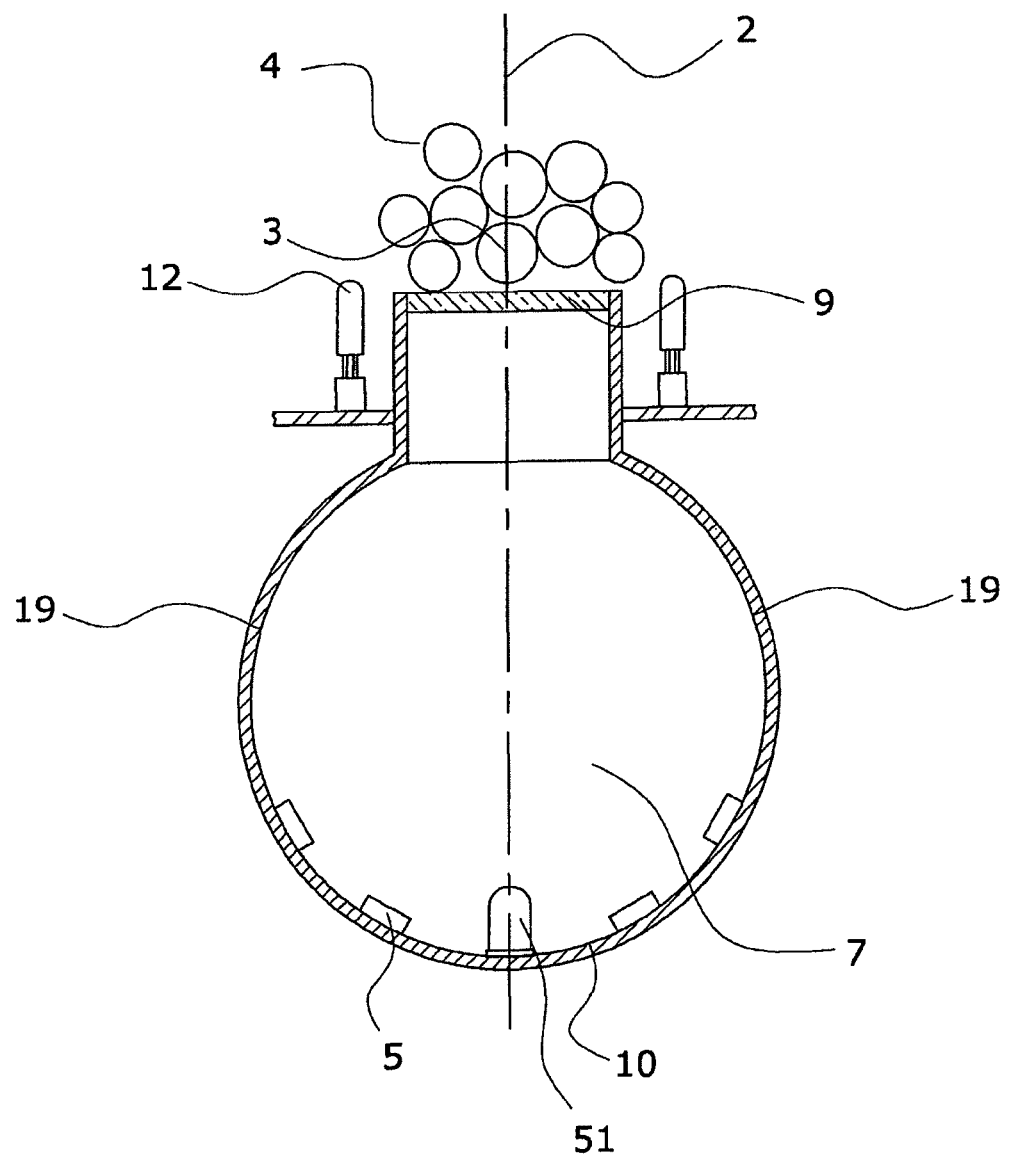
Figure 12:
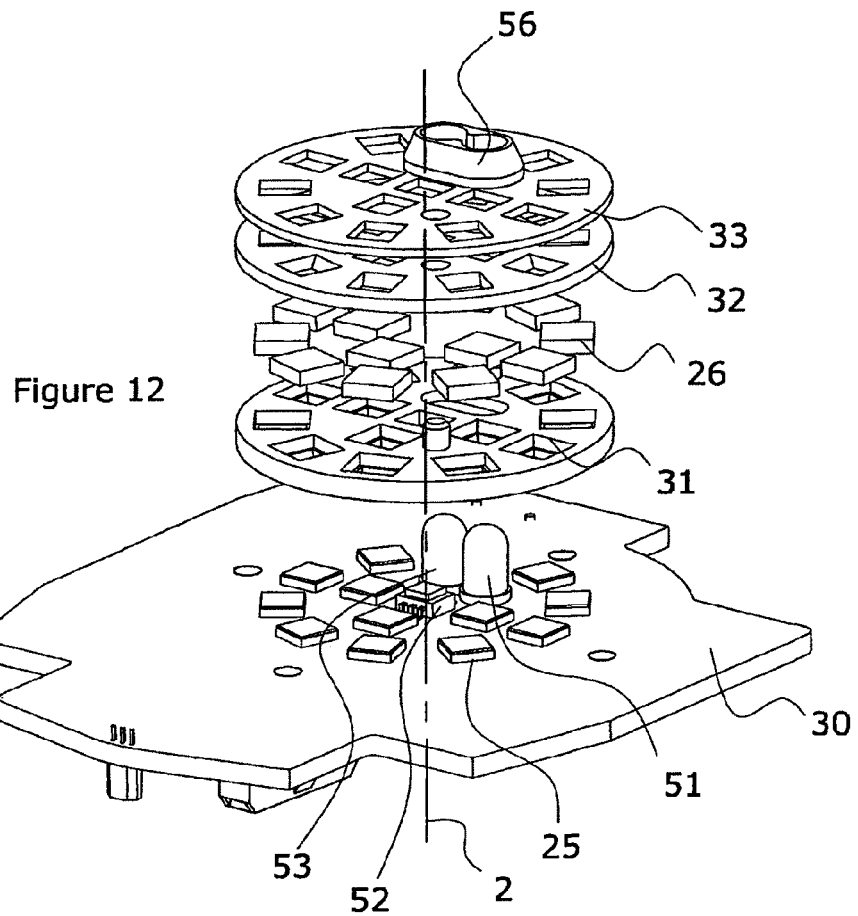
FIGS. 12 and 13 illustrate perspective views showing a device, exploded and assembled, respectively, for mounting the optical sensors, according to a first embodiment.
Figure 13:
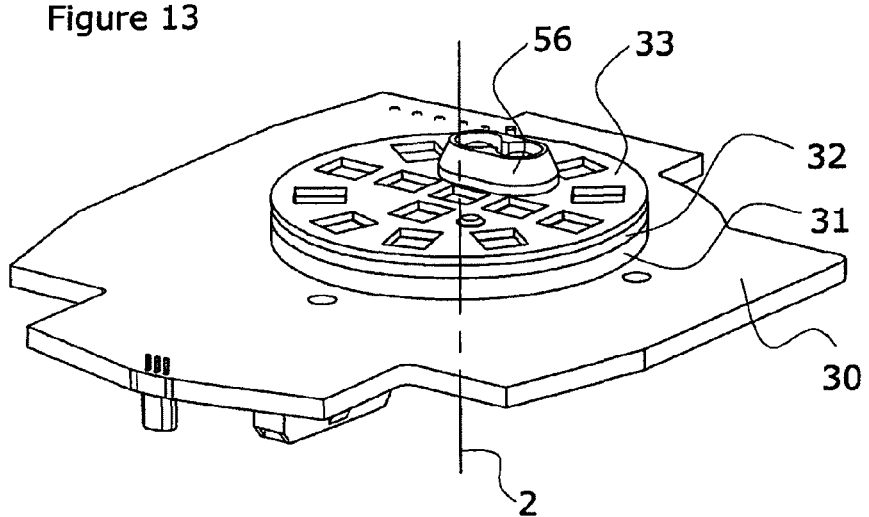

According to a second embodiment, the fourth illumination device 53 and the optical color sensor 54 are arranged between the scatter filter 9 and the lens 55. Such a configuration is shown in FIG. 5.

The principle of the fluorescence is to illuminate a sample 4 with a light including at least one first wavelength particularly selected to cause, in the presence of a particular reactive compound, a return light emission along a second wavelength. The fourth illumination device 53 is then a monochromatic luminous source centered on said first wavelength, or whose spectrum includes at least this wavelength. The specific optical sensor 54 is then a sensor sensitive to the second wavelength, such as, for example, a photodiode equipped with a spectral optical band-pass filter centered on said second wavelength.

Thus, a particular application, in the illustrative example directed to vine and grapes, is the detection of a parasitic fungus called botrytis. This fungus has a fluorescence effect. When illuminated by a monochromatic light having a central wavelength 380 nm, the botrytis reacts by reemitting a light radiation having a central wavelength 522 nm, detectable with a specific optical sensor 54 centered on this wavelength. An illumination including the wavelength 380 nm can be achieved by means of a UV LED producing a spectrum of 380 nm+/−15 nm.

To coordinate the various components and to carry out the measurements, the optical spectrometer 1 further includes a logic processing unit 60. The latter is typically arranged around a calculator system having a microprocessor or microcontroller, equipped with peripheral devices, operating under the control of software. This logic processing unit 60 is interfaced with the various electrical devices: illumination devices 12, 50, 51, 53 and optical sensors 5, 52, 54. Thus, said logic processing unit 60 is adapted to control the selective switching on of the illumination devices 12, 50, 51, 53. It is also capable of acquiring measurements from the various optical sensors 5, 52, 54 and their signal processing chains 40, 41, 42. It is also capable of producing determinations by calculation from the measurements coming from said optical sensors 5, 52, 54. It is also capable of storing and restoring such measurements and determinations.

The optical spectrometer 1 further includes a man-machine interface 61, interfaced with said logic processing unit 60. This man-machine interface 61 includes at least one input means 62 and an output means 63. An input means 62 is typically a button, a keyboard or a trigger 62, adapted to enable a user of the optical spectrometer 1 to initialize a program for performing a sequence of measurements, for example according to the method which is described hereinafter. An output means 63 is typically a display, for example a screen 63 adapted to display the measurement results. Other input means can be present in order, for example, to make it possible to configure the optical spectrometer 1.

There is at least one storage means 64 among the peripheral devices of the logic processing unit. This means can include an internal memory, removable if necessary, in the form, for example, of a flash memory card, in order to be able to transmit measurements or determinations to another storage or processing unit. It is possible to provide redundancy to this storage means to ensure a backup of the measurements and determinations. Thus, any measurement can be stored concurrently in an internal resident memory of the flash or EEPROM type, for example, and redundantly on a removable memory of the SD memory card type, for example.

A transmission means 65 can also be provided. This transmission means 65 can include a wire link (RS, Ethernet, parallel, USB, etc.) or a microwave link (WiFi, GSM, GPRS, Bluetooth, etc.). The advantage of a microwave link is in being able to transmit the measurements performed in the field almost immediately to a central storage and processing unit.

Thus, in the illustrative example applied to grapes, one or more spectrometers perform compound content measurements in the rows of a vineyard. These measurements are transmitted to a central logic processing unit located in the wine storehouse, for example, which compiles all the measurements to produce more comprehensive results. Thus, for example, the content measurements can be fed into an application for predicting the optimum date for the harvest.

The optical spectrometer 1 can further include a geolocation device 66. This device 66 may be a GPS receiver, a GPRS receiver, or an equivalent. It is advantageously interfaced with the logic processing unit 60, to which it supplies locations and, if necessary, a precise date/time. Thus, the logic processing unit 60 can advantageously associate a measurement with its geographical location and/or date/time, at the time the measurement or determination is being carried out. This is advantageous in mapping the measurements in various areas of a facility or a farm.

Figure 18:
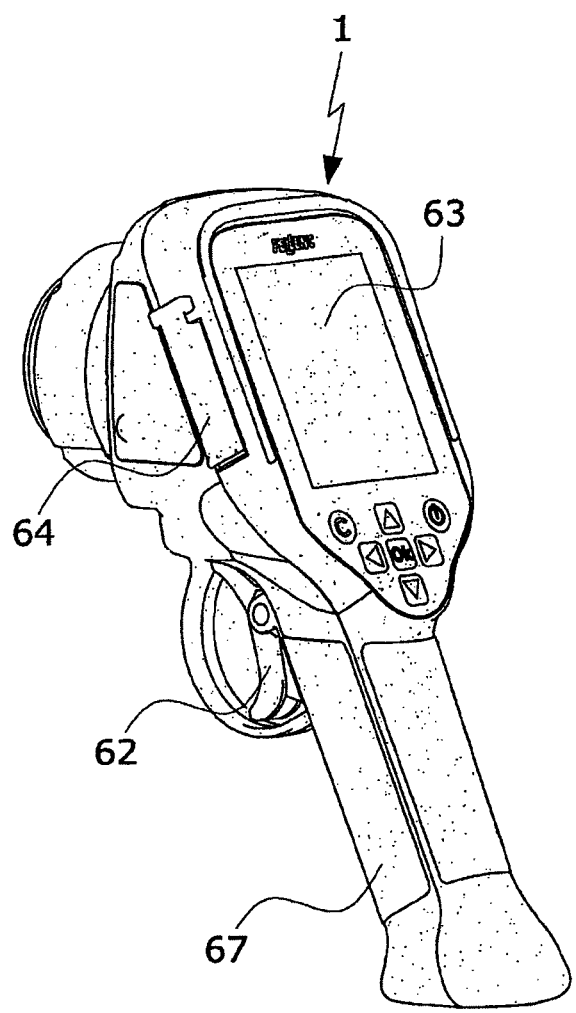
FIG. 18 shows a perspective view of the spectrometer.
Figure 19:
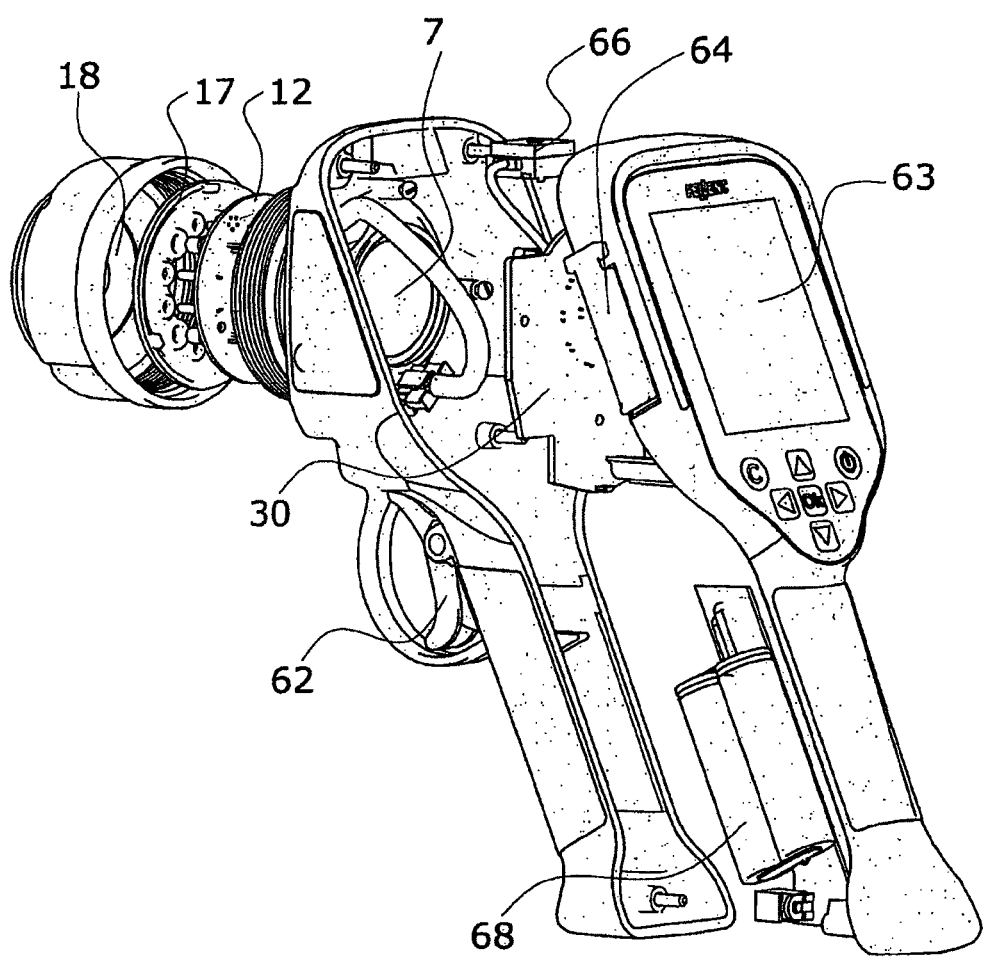
FIG. 19 shows an exploded perspective view of the same spectrometer.
Figure 20:
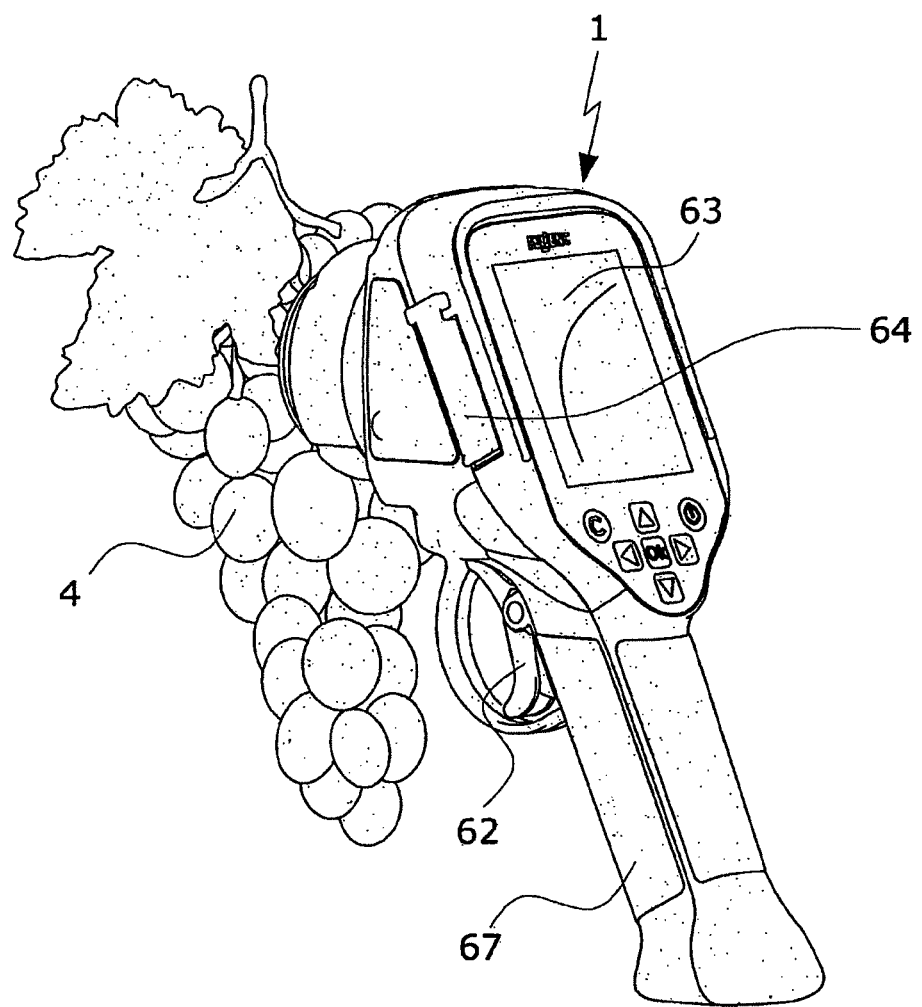
FIGS. 20 and 21 show two examples of use of the spectrometer.
Figure 21:
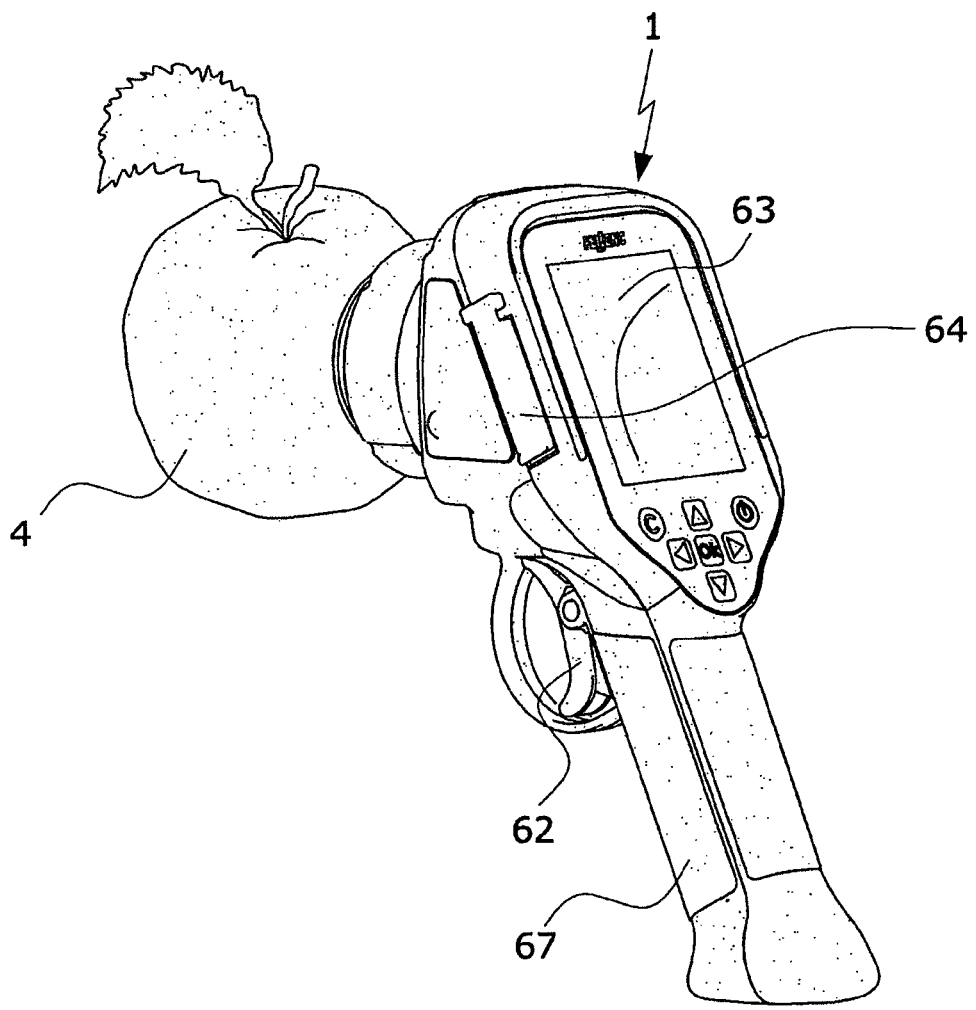

The optical spectrometer 1 is advantageously portable, in that all of its components can be sufficiently small in size. The electric autonomy is ensured by a battery 68 integrated into the device. FIGS. 18 and 19 show an example of embodiment that can be carried out by means of a handle 67 and operated with one hand by an operator, who can use his free hand to present the sample 4 in the target zone 3.

The invention further relates to a method for using an optical spectrometer 1 of the aforementioned type. Acquisitions are made to obtain measurements. A first measurement is performed, using the optical sensors 5, in the presence of a sample 4, the compound contents of which are to be determined, the sample 4 being positioned in the target zone 3. During measurement, the sample 4 is illuminated by the main illumination device 12, only the latter being switched on, excluding the reference illumination device 50, the third illumination device 51 and the fourth illumination device 53, if they are present. Each of the optical sensors 5, substantially at the same time, carries out a measurement $m_i$, where the index i defines all of the optical sensors 5, including n elements. This measurement is called a "real" measurement.

To improve the quality of the measurement, another measurement is carried out by the same optical sensors 5, all of the illumination devices, including the main illumination device 12, the reference illumination device 50, the third illumination device 51, and the fourth illumination device 53 being switched off. The presence of the sample 4 is advantageous in this case in making it possible to compare the various measurements. Therefore, these various measurements are preferably made in a short time interval, their relative order is immaterial. Each of the optical sensors 5 acquires, substantially at the same time, a measurement $b_i$, where the index i defines all of the optical sensors 5, including n elements. This measurement is called a "black" measurement. It is indicative of the optical background noise of the sensors and of the environment, and is then removed from the other measurements.

A compensation device is used to further improve the quality of the measurement, by overcoming the changes, over time, in the quality of the spectrum emitted by the main illumination device 12 (thermal drift as a function of its own temperature, thermal drift as a function of room temperature, aging, etc). The reference illumination device 50, already described, is designed to produce a spectrum which, even if slowly changing over time, remains at all times identical to the spectrum of the main illumination device 12. This allows for compensation by comparing a measurement carried out by analyzing the light from the main illumination device 12 after backscattering by the sample 4 and a measurement carried out by analyzing the light, theoretically identical, directly from the reference illumination device 50. Once again, the various measurements are preferably performed in a short time interval, but their order is immaterial.

To obtain this second measurement, a measurement is carried out by the same optical sensors 5, only the reference illumination device 50 being switched on. The other illumination devices, including the main illumination device 12, the third illumination device 51 and the fourth illumination device 53, are switched off. The presence of sample 4 is still necessary in this case to produce comparable conditions. Each of the optical sensors 5 performs, substantially at the same time, a measurement $r_i$, where the index i defines all of the optical sensors 5, including n elements. This measurement is called a "reference" measurement. It is indicative of the spectrum of the illumination light when it is not modified by the sample 4. This measurement $r_i$ can be further improved by removing the "black" measurement $b_i$ therefrom.

From these three measurements, a corrected value $X_i$ is determined, for i between 1 and n, by removing the "black" measurement $b_i$ from each of the other two measurements $m_i$ and $r_i$, and by comparing the two by a quotient relating the "real" measurement to the "reference" measurement. This can be expressed by the following formula:

$$X_i = \frac{m_i - b_i}{r_i - b_i}.$$

The compensation for the various illumination drifts by using a reference illumination device 50 and comparing the measurements, as described, advantageously makes it possible to achieve compensation in a simple fashion, including under the inevitably variable conditions encountered in the field. Conversely, laboratory equipment uses a calibrated light source that is well known and reproducible, and/or an enclosure that is thermally controlled in a precise manner in order to remove any cause of drift. Such means are not transferable to a portable field optical spectrometer such as that of the invention.

The method further includes a second derivation step in which $D_i$ are calculated, for i between 1 and n. This step applies the formulas:

$$D_1 = 2(X_1 - X_2).$$

$$D_i = 2X_i - X_{i-1} - X_{i+1} \text{ for i between 2 and } n-1,$$

$$D_n = 2(X_n - X_{n-1}).$$

In a following step, the method further includes a normalization step using a standard equal to the sum of squares $$\sum_{i=1}^{N} (D_i)^2$$

in order to obtain a plurality of $N_i$, using the formula:

$$N_i = \frac{D_i}{\sqrt{\sum_{i=1}^{n} (D_i)^2}},$$

for i between 1 and n.

In a following step, the method further includes a step in which the $N_i$ from the measurements are then transformed by linear combination, in order to determine the compound contents $M_j$ in the sample 4 using the formula:

$$M_j = SM_{jn+1} + \sum_{i=1}^{n} N_i \cdot SM_{ji},$$

where:

$N_i$ is the number previously determined from the n measurements $X_i$ coming from the optical sensors, i between 1 and n, n being the number of optical sensors 5, $M_j$ is the content of the $j^{th}$ compound, j between 1 and p, p being the number of compounds, $SM_{ji}$ is a characteristic coefficient.

The $SM_{ji}$ are a set of characteristic coefficients of the p compounds, the contents of which one wishes to measure, and of the n optical sensors 5 or equivalent, of the n wavelengths associated with these optical sensors. The matrix SM having a dimension [n+1, p] of the coefficients $SM_{ji}$ is thus characteristic of the coupling between these wavelengths and said compounds. The matrix SM is thus a characteristic of the configuration of a spectrometer 1 according to the invention and of the method for using it. It is stored in the memory of the logic processing unit 60. The change of destination for the spectrometer, to enable it to determine the contents of other compounds, requires a reconfiguration that includes the modification of the wavelengths (their number, if necessary), which can be achieved by modifying the optical filters 26, and the concomitant modification of the matrix SM, which can be carried out by modification in the memory of the logic processing unit 60. A method for determining this characteristic matrix SM will now be described.

The matrix of coefficients $SM_{ji}$ establishes a linear relation between the contents $M_j$ of the compounds, j defining all of the p compounds, and the determinations $N_i$, i defining all of the n optical sensors 5, calculated from the measurements made by the n optical sensors 5. The relation is expressed as $$M_j = SM_{jn+1} + \sum_{i=1}^{n} N_i \cdot SM_{ji},$$

or an affine linear relation, where $SM_{ji}$, for i between 1 and n is a weight assigned to the $i^{th}$ optical sensor 5, for determining the content of the $j^{th}$ compound, and $SM_{jn+i}$ is an additional offset term.

The coefficients $SM_{ji}$ of this relation are identified by any known method, from a series of measurements on samples 4, performed with the spectrometer according to the invention to determine the $N_i$, the contents $M_j$ of these same samples being known, for example by means of a measurement carried out using a laboratory spectrometer. An applicable known method is the multiple linear regression.

Figures 23, 24:
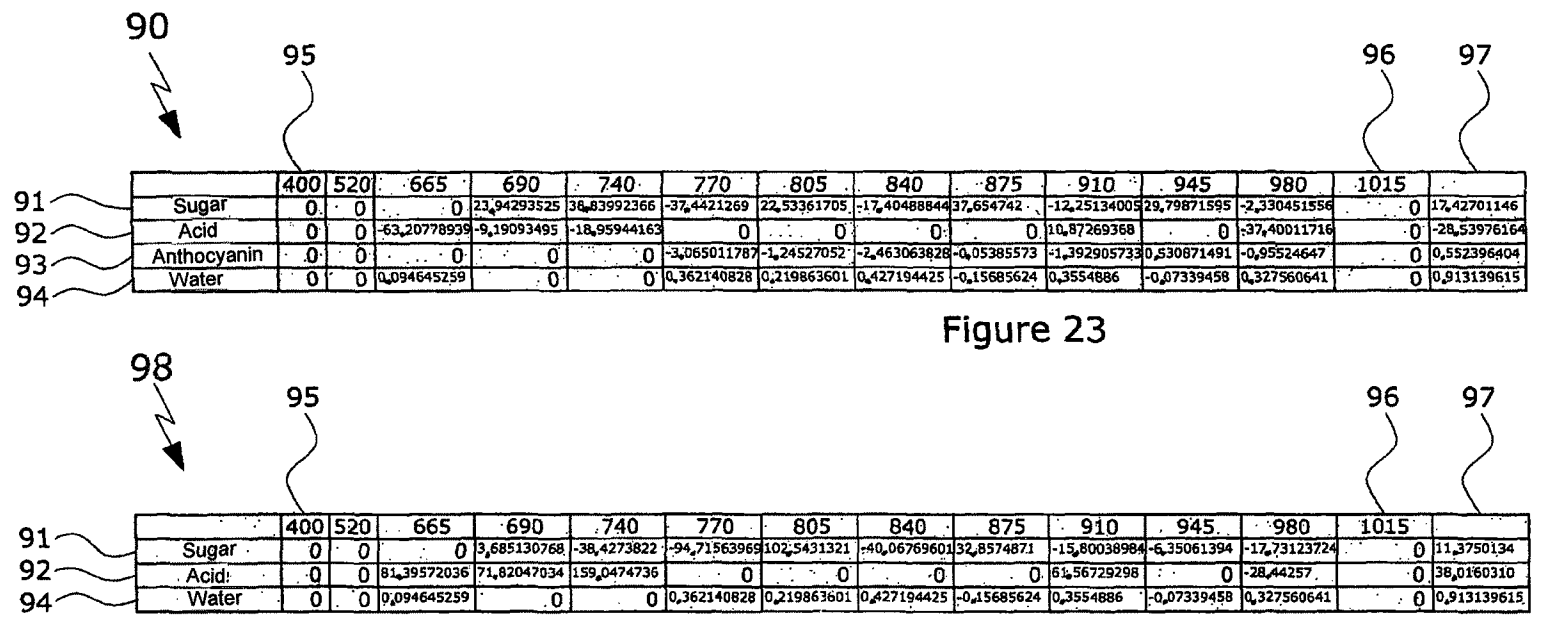

According to a particular illustrative embodiment, applied to grapes, one wishes to determine the contents of the following four compounds: water, sugar, polyphenols anthocyanins and acid. For these compounds, and for the associated lengths retained, namely n=13 wavelengths (440, 520, 665, 690, 740, 770, 805, 840, 875, 910, 945, 980, 1015), two examples of matrix SM are shown in FIGS. 23 and 24. The matrix SM (90) of FIG. 23 is applicable to black/red grapes, and the matrix SM (98) of FIG. 24 is applicable to white grapes. The first 90 of these matrices includes four rows 91 to 94 corresponding to the 4 compounds sugar, acid, anthocyanin and water, respectively. The second 98 of said matrices comprises only three rows, since the anthocyanin compound does not exist for white grapes. It also includes 14 columns. The first 13 columns, including the first column 95 and last column 96, correspond to the 13 optical sensors. An additional column 97 contains the offset coefficients $SM_{jn+1}$.

The method optionally further includes a measurement of the color of the sample 4, in the same measurement sequence, in order to take advantage of the presence of the sample 4 in the target zone 3. To this end, an acquisition is made using the optical color sensor 52, only the third illumination device 51 being switched on to illuminate the sample 4. This makes it possible to obtain a "real color" measurement $m_c$ of the color of the sample 4.

As with the other measurements made by the optical sensors 5 dedicated to the determination of the compound contents, this measurement can be corrected by subtraction of a "black" measurement and by compensation using a "reference" measurement.

The method further includes a step of obtaining of a "reference color" measurement $r_c$, by acquisition using the optical color sensor 52, only the reference illumination device 50 being switched on. Thus, the optical color sensor 52 is illuminated directly without modification caused by the backscatter from the sample 4.

Similarly, a "black color" measurement $b_c$ is performed by acquisition using the optical color sensor 52, all of the illumination devices 12, 50, 51, 53 being switched off.

A step is then undertaken to determine a corrected color value $X_c$, according to the formula:

$$X_c = \frac{m_c - b_c}{r_c - b_c}.$$

The method optionally further includes a fluorescence measurement of the sample 4, in the same measurement sequence, in order to take advantage of the presence of the sample 4 in the target zone 3. To this end, an acquisition is made using the specific optical sensor 54, only the fourth illumination device 53 being switched on to illuminate the sample 4 with a light including at least one first particular wavelength. This makes it possible to obtain a "real fluorescence" measurement $m_f$ of the sample 4.

As with other measurements made by the optical sensors 5, 52, this measurement can be corrected by subtraction of a "black" measurement. Compensation by means of a "reference" measurement is not applicable.

The method further includes a step of obtaining a "black fluorescence" measurement $b_f$ carried out by acquisition using the specific optical sensor 54, all of the illumination devices 12, 50, 51, 53 being switched off.

A step is then undertaken to determine a corrected fluorescence value $X_f$ according to the formula $X_f = m_f - b_f$.

In order to overcome a possible anomaly localized on a single acquisition, it is advantageous to replace a single acquisition by a multiple acquisition followed by an averaging of these acquisitions. Thus, the "real" $m_i$, "real color" $m_c$, "real fluorescence" $m_f$, "reference" $r_i$, "reference color" $r_c$, "black" $b_i$, "black color" $b_c$, "black fluorescence" $b_f$ measurement, respectively, is advantageously obtained by performing a plurality of q acquisitions, and by obtaining an average of these q acquisitions, said average being then used as a measurement.

The number of q acquisitions must be sufficiently large to avoid the anomalies, while remaining sufficiently small not to unduly lengthen the duration of the measurement sequence. Given the frequencies of the conventional acquisition devices, a number of repetitions q=100 is adequate.

Figure 22:
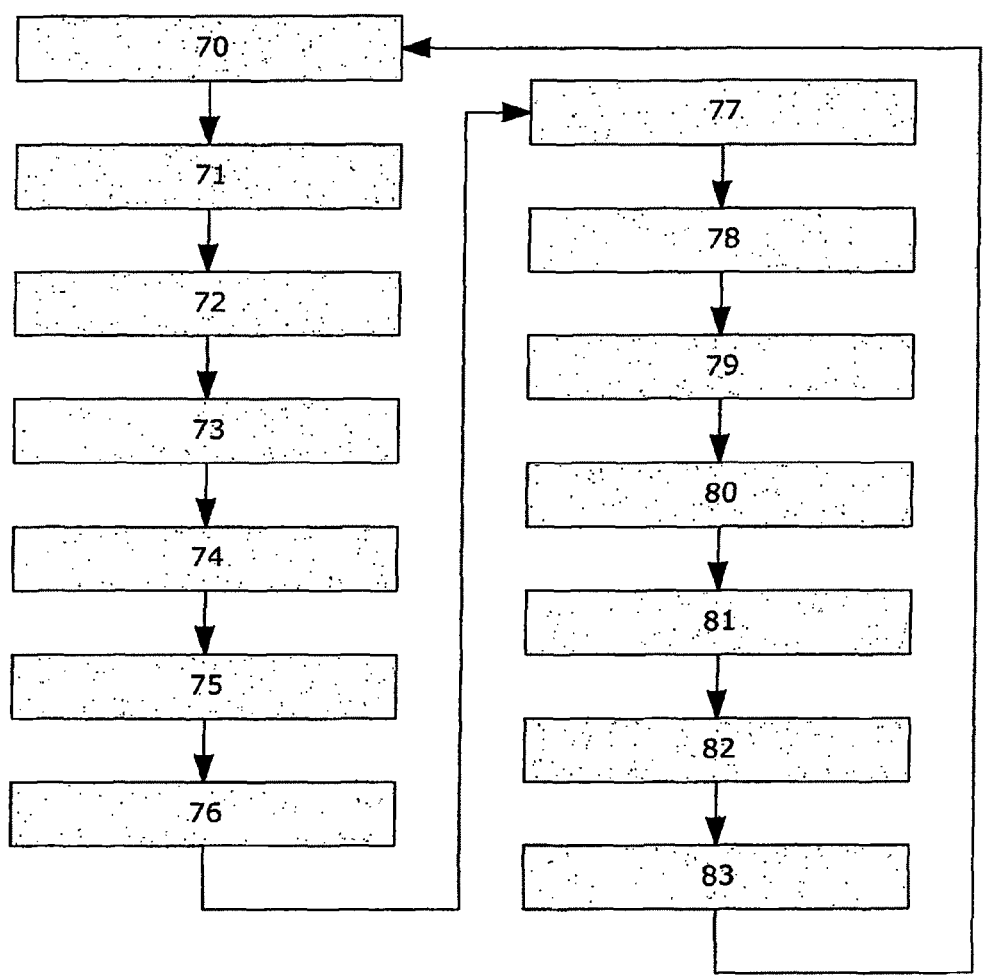
FIG. 22 shows a measurement sequence flowchart.

Reference is made to FIG. 22 to describe a method of use being carried out. A typical measurement sequence is initiated, for example, by actuating the trigger-type input means 62 of the man-machine interface 61. The various acquisition operations, accompanied by the controls for the corresponding illumination devices, are undertaken in any order. The various processing operations can then be undertaken to produce the final determinations, namely the p compound contents and, if necessary, the color and presence/amount of the compound detected by fluorescence. These values can be displayed on the output means 63 of the man-machine interface 61.

An illustrative example of measurement sequence (FIG. 22) includes the following successive operations:

70 pressing the trigger 70,
71 performing "black" measurement $n_i$, i between 1 and n, $n_c$ and $n_f$,
72 switching on the reference illumination device 50,
73 performing "reference" measurement $r_i$, i between 1 and n, and $r_c$,
74 switching off the reference illumination device 50,
75 switching on the main illumination device 12,
76 waiting 200 ms,
77 performing "real" measurement $m_i$, i between 1 and n, $m_c$, and $m_f$,
78 switching off the main illumination device 12,
79 calculations of the $X_i$, i between 1 and n, $X_c$, $X_f$,
80 storage in memory,
81 calculations of the $D_i$ and $N_i$, i between 1 and n, and of the $M_j$, j between 1 and p,
82 display of the results,
83 waiting to press the trigger.

The presence of a logic processing unit 60 is advantageous in that it allows for various processing operations on the measurements obtained. Other determinations can be calculated and, if necessary, displayed on the output means 63.

Thus, in addition to the instantaneous measurements and determinations already mentioned, it is possible to determine an average of the time of the instantaneous measurements and determinations obtained for various samples 4 analyzed successively.

During a measurement sequence, it is still possible to determine a confidence index based, for example, on the standard deviation of a measurement. The display of this confidence index, intended for the operator, enables the latter to determine whether to continue or to shorten the measurement session.

A go/no-go acceptance test can be performed for a measurement sequence. For one type of product to be analyzed and a given configuration of the spectrometer 1 (wavelengths, set of compounds), possible extreme values of the various measurements and determinations are known. A sample or a measurement sequence that would produce one or more measurements outside of these extreme values would lead to a rejection of the sequence. This makes it possible to avoid sequences that are distorted by a sample 4 that is unsuitable, incorrectly positioned in the target zone 3, or by an optical anomaly. An example of optical anomaly is a measurement that would be carried out by pointing the spectrometer 1 toward an intense light source, like the sun. Such a measurement would be completely distorted by a blinding of the highly sensitive optical sensors.

The method can also include a storage step, undertaken as soon as the measurements and determinations are completed. This storage can be local on an internal storage means 64 residing in the spectrometer and/or on a removable means such as a memory card. It is also possible to perform an alternative or complementary step of transmitting to another logic processing unit, either in real time as soon as the measurement or determination is available, or delayed in batches.

The measurement sequence can further include the determination of a position using the geolocation device 66. This position can advantageously be associated with a measurement or a determination made at that position.

The invention claimed is:

1. An optical spectrometer structured to analyze a light spectrum backscattered by an illuminated sample, in order to deduce the content of at least one constituent compound of the sample, the spectrometer being arranged about an optical axis and comprising:
a target zone, centered on the optical axis, being structured and arranged to receive the sample;
a plurality of sensors including at least one optical sensor trained on the target zone;
a main illumination device structured and arranged to illuminate the sample;
a light-opaque measurement chamber comprising:
an opening centered on the optical axis,
at least one scatter filter blocking the opening, an inner bottom, centered on the optical axis, being structured and arranged to receive the plurality of optical sensors, wherein the target zone is located in a vicinity of the opening, outside of the measurement chamber and wherein the main illumination device is arranged, relative to a plane perpendicular to the optical axis passing via the scatter filter, on a side opposite the target zone.

2. The optical spectrometer according to claim 1, wherein the main illumination device is arranged annularly about the optical axis and is covered with a translucent and optically neutral protection.

3. The optical spectrometer according to claim 1, wherein an opening angle of the measurement chamber, from the opening, is less than or equal to the scatter angle of the scatter filter, and the inner bottom and an inner lateral wall of the measurement chamber are structured to be optically absorbent.

4. The optical spectrometer according to claim 1, wherein the inner bottom has one of a spherical shape centered on the target zone or a planar shape perpendicular to the optical axis.

5. The optical spectrometer according to claim 4, wherein the inner bottom has the planar shape perpendicular to the optical axis and a wavelength associated with an optical sensor is offset so as to compensate for an axial misalignment of the optical sensor relative to an axis trained on the target zone caused by the planar shape of the inner bottom.

6. The optical spectrometer according to claim 1, wherein the measurement chamber has a photometric gain G at least equal to 4, which is defined by the formula:

$$G = 100 \cdot \left(\frac{\Phi}{L}\right)^2,$$

in which
$\Phi$: the diameter of the opening, and
L: the distance between the opening and the inner bottom.

7. The optical spectrometer according to claim 1, wherein each of the optical sensors of the plurality sensors is structured and arranged to measure a luminous intensity along a given wavelength and includes a photodiode and an optical filter arranged in front of a sensitive surface of the photodiode, the photodiode being a large area photodiode, the optical filter being a band-pass filter centered on the given wavelength and an amplifier/filter structured to have a gain adjustable to maximize the excursion of the luminous intensity measurement.

8. The optical spectrometer according to claim 1, further comprising a reference illumination device structured to reproduce luminous characteristics of the main illumination device and arranged outside of the measurement chamber to directly illuminate the inner bottom through the scatter filter.

9. The optical spectrometer according to claim 1, further comprising a system for measuring a color of the sample that includes a third illumination device and an optical color sensor, wherein both the third illumination device and the optical color sensor are trained on the target zone and are arranged on the inner bottom and substantially on the optical axis.

10. The optical spectrometer according to claim 1, further comprising a system for fluorescence measurement of the sample that includes a fourth illumination device and a specific optical sensor, wherein both the fourth illumination device and a specific optical sensor are trained on the target zone and are arranged on the inner bottom and substantially on the optical axis, and wherein the specific optical sensor has a central wavelength of 522 nm, in order to allow detection of the Botrytis.

11. The optical spectrometer according to of claim 1, further comprising a geolocation device structured and arranged to measure a position, and a mechanism structured and arranged to associate the position with each measurement or determination made at that position.

12. The optical spectrometer according to claim 1 being self-contained and portable.

13. A method for using an optical spectrometer structured to analyze a light spectrum backscattered by an illuminated sample, in order to deduce the content of at least one constituent compound of the sample, the spectrometer being arranged about an optical axis and including: a target zone, centered on the optical axis, being structured and arranged to receive the sample, a plurality of sensors including at least one optical sensor trained on the target zone; a main illumination device structured and arranged to illuminate the sample; a light-opaque measurement chamber comprising: an opening centered on the optical axis, at least one scatter filter blocking the opening an inner bottom centered on the optical axis, being structured and arranged to receive the plurality of optical sensors, such that the target zone is located in a vicinity of the opening, outside of the measurement chamber, the method comprising:

acquiring a "real" measurement $m_i$ in a presence of the sample in the target zone, when only the main illumination device is switched on to illuminate the sample, wherein i defines a number of optical sensors from 1 to n included in the plurality sensors;

acquiring a "black" measurement b when all of the illumination devices are switched off; and acquiring a "reference" measurement $r_i$ when only the reference illumination device is switched on to directly illuminate said optical sensors.

14. The method according to claim 13, further comprising at least one of:

determining a corrected value $X_i$ for i between 1 and n, such that $$X_i = \frac{m_i - b_i}{r_i - b_i},$$

a second derivation step to obtain $D_i$ for i between 1 and n, such that $D_1 = 2(X_1 - X_2)$, $D_i = 2X_i - X_{i-1} - X_{i+1}$ for i between 2 and n−1, and $D_n = 2(X_n X_{n-1})$, a normalization step to obtain $N_i$, for i between 1 and n, such that $$N_i = \frac{D_i}{\sqrt{\sum_{i=1}^{n}(D_i)^2}};$$

and determining a compound content $M_j$ in the sample, where j defines from 1 to p all of the compounds, the contents of which are measured by application of the formula:

$$M_j = SM_{jn+1} + \sum_{i=1}^{n} N_i \cdot SM_{ji}$$

where $SM_{ji}$ is a characteristic coefficient.

15. The method according to claim 13, further comprising at least one of:
   obtaining a "real color" measurement $m_c$ of the color of the sample using an optical color sensor when a third illumination device is switched on to illuminate the sample;
   acquiring a "reference color" measurement $r_c$ using an optical color sensor when the reference illumination device is switched on to directly illuminate the optical color sensor;
   acquiring a "black color" measurement $b_c$ using an optical color sensor when all of the illumination devices are switched off; and
   determining a corrected color value $X_c$, in which $$X_c = \frac{m_c - b_c}{r_c - b_c}.$$

16. The method according to claim 13, further comprising at least one of:
   obtaining a "real fluorescence" measurement $m_f$ of sample using a specific optical sensor when a fourth illumination device is switched on to illuminate the sample;
   acquiring a "black fluorescence" measurement $b_f$ using the specific optical sensor when all of the illumination devices are switched off; and
   determining a corrected fluorescence value $X_f$, in which $X_f = m_f - b_f$.

* * * * *